(12) United States Patent
Berman et al.

(10) Patent No.: US 10,603,040 B1
(45) Date of Patent: *Mar. 31, 2020

(54) METHODS FOR TREATING HYPERTENSION AND REDUCING BLOOD PRESSURE WITH FORMATION OF FISTULA

(71) Applicant: TVA Medical, Inc., Austin, TX (US)

(72) Inventors: Adam L. Berman, Austin, TX (US);
William E. Cohn, Bellaire, TX (US);
Dana R. Mester, Austin, TX (US);
Damian A. Jelich, Austin, TX (US);
Thomas D. Pate, Austin, TX (US);
Philip M. Tetzlaff, Austin, TX (US)

(73) Assignee: TVA MEDICAL, INC., Franklin Lakes, NJ (US)

( * ) Notice: Subject to any disclaimer, the term of this patent is extended or adjusted under 35 U.S.C. 154(b) by 430 days.

This patent is subject to a terminal disclaimer.

(21) Appl. No.: 15/019,962

(22) Filed: Feb. 9, 2016

Related U.S. Application Data

(60) Provisional application No. 62/114,040, filed on Feb. 9, 2015.

(51) Int. Cl.
*A61B 17/11* (2006.01)
*A61B 18/14* (2006.01)
*A61B 18/00* (2006.01)

(52) U.S. Cl.
CPC .......... *A61B 17/11* (2013.01); *A61B 18/1492* (2013.01); *A61B 2017/1103* (2013.01);
(Continued)

(58) Field of Classification Search
CPC .. A61B 2017/1107; A61B 2018/00577; A61B 17/11; A61B 2018/1497;
(Continued)

(56) References Cited

U.S. PATENT DOCUMENTS 3,649,850 A   3/1972 Davis
3,827,436 A   8/1974 Stumpf et al.
(Continued)

FOREIGN PATENT DOCUMENTS

CA    2883209 A1 *  4/2014  ............. A61B 17/11
CN    1730123 A     2/2006
(Continued)

OTHER PUBLICATIONS

Hakim et al., "Ulnar artery-based free forearm flap: Review of Specific anatomic features in 322 cases and related literature," Heand & Neck, Dec. 2013 (published online:2014), Wiley Online Library.*

(Continued)

*Primary Examiner* — Jaymi E Della
*Assistant Examiner* — Christine A Dedoulis
(74) *Attorney, Agent, or Firm* — Dinsmore & Shohl LLP

(57) ABSTRACT

Described here are devices and methods for treating hypertension by forming a fistula between two blood vessels to reduce blood pressure of a patient. The fistula may be formed using a catheter having an electrode that is placed in a first blood vessel. In some instances, a desired amount of blood pressure is determined. In other instances, the hypertension is drug resistant hypertension.

5 Claims, 19 Drawing Sheets

(52) U.S. Cl.
CPC .......... *A61B 2017/1107* (2013.01); *A61B 2017/1139* (2013.01); *A61B 2018/00404* (2013.01); *A61B 2018/00577* (2013.01)

(58) Field of Classification Search
CPC .......... A61M 2025/0166; A61M 25/00; G09B 19/00; G09B 23/28; G06G 7/48
See application file for complete search history.

(56) References Cited

U.S. PATENT DOCUMENTS

| | | | |
|---|---|---|---|
| 4,416,664 | A | 11/1983 | Womack |
| 4,802,475 | A | 2/1989 | Weshahy |
| 5,313,943 | A | 5/1994 | Houser et al. |
| 5,697,909 | A | 12/1997 | Eggers et al. |
| 5,800,487 | A | 9/1998 | Mikus et al. |
| 5,830,222 | A | 11/1998 | Makower |
| 5,830,224 | A * | 11/1998 | Cohn ............... A61B 17/11 604/22 |
| 5,895,404 | A | 4/1999 | Ruiz |
| 5,971,979 | A | 10/1999 | Joye et al. |
| 6,004,330 | A | 12/1999 | Middleman et al. |
| 6,032,677 | A | 3/2000 | Blechman et al. |
| 6,039,730 | A | 3/2000 | Rabin et al. |
| 6,068,638 | A | 5/2000 | Makower |
| 6,099,542 | A | 8/2000 | Cohn et al. |
| 6,159,225 | A | 12/2000 | Makower |
| 6,190,353 | B1 | 2/2001 | Makower et al. |
| 6,197,025 | B1 | 3/2001 | Grossi et al. |
| 6,217,575 | B1 | 4/2001 | DeVore et al. |
| 6,231,587 | B1 | 5/2001 | Makower |
| 6,256,525 | B1 | 7/2001 | Yang et al. |
| 6,283,988 | B1 | 9/2001 | Laufer et al. |
| 6,287,306 | B1 | 9/2001 | Kroll et al. |
| 6,302,875 | B1 | 10/2001 | Makower et al. |
| 6,327,505 | B1 | 12/2001 | Medhkour et al. |
| 6,347,247 | B1 | 2/2002 | Dev et al. |
| 6,355,029 | B1 | 3/2002 | Joye et al. |
| 6,357,447 | B1 | 3/2002 | Swanson et al. |
| 6,379,353 | B1 | 4/2002 | Nichols |
| 6,383,180 | B1 | 5/2002 | LaLonde et al. |
| 6,400,976 | B1 | 6/2002 | Champeau |
| 6,428,534 | B1 | 8/2002 | Joye et al. |
| 6,461,356 | B1 | 10/2002 | Patterson |
| 6,464,665 | B1 | 10/2002 | Heuser |
| 6,464,723 | B1 | 10/2002 | Callol |
| 6,468,268 | B1 | 10/2002 | Abboud et al. |
| 6,475,214 | B1 | 11/2002 | Moaddeb |
| 6,475,226 | B1 | 11/2002 | Belef et al. |
| 6,527,724 | B1 | 3/2003 | Fenici |
| 6,527,769 | B2 | 3/2003 | Langberg et al. |
| 6,542,766 | B2 | 4/2003 | Hall et al. |
| 6,544,230 | B1 | 4/2003 | Flaherty et al. |
| 6,569,158 | B1 | 5/2003 | Abboud et al. |
| 6,569,162 | B2 | 5/2003 | He |
| 6,579,311 | B1 | 6/2003 | Makower |
| 6,585,650 | B1 | 7/2003 | Solem |
| 6,592,577 | B2 | 7/2003 | Abboud et al. |
| 6,635,053 | B1 | 10/2003 | LaLonde et al. |
| 6,655,386 | B1 | 12/2003 | Makower et al. |
| 6,656,173 | B1 | 12/2003 | Palermo |
| 6,663,625 | B1 | 12/2003 | Ormsby et al. |
| 6,669,709 | B1 | 12/2003 | Cohn et al. |
| 6,676,657 | B2 | 1/2004 | Wood |
| 6,682,525 | B2 | 1/2004 | LaLonde et al. |
| 6,695,878 | B2 | 2/2004 | McGuckin et al. |
| 6,709,444 | B1 | 3/2004 | Makower |
| 6,719,756 | B1 | 4/2004 | Muntermann |
| 6,726,697 | B2 | 4/2004 | Nicholas et al. |
| 6,733,494 | B2 | 5/2004 | Abboud et al. |
| 6,736,808 | B1 | 5/2004 | Motamedi et al. |
| 6,761,708 | B1 | 7/2004 | Chiu |
| 6,761,714 | B2 | 7/2004 | Abboud et al. |
| 6,780,181 | B2 | 8/2004 | Kroll et al. |
| 6,849,073 | B2 | 2/2005 | Hoey et al. |
| 6,855,143 | B2 | 2/2005 | Davison et al. |
| 6,887,234 | B2 | 5/2005 | Abboud et al. |
| 6,911,026 | B1 | 6/2005 | Hall et al. |
| 6,932,814 | B2 | 8/2005 | Wood |
| 6,936,024 | B1 | 8/2005 | Houser |
| 6,960,209 | B2 | 11/2005 | Clague et al. |
| 6,971,983 | B1 | 12/2005 | Cancio |
| 6,981,972 | B1 | 1/2006 | Farley et al. |
| 7,059,330 | B1 | 6/2006 | Makower et al. |
| 7,060,063 | B2 | 6/2006 | Marion et al. |
| 7,094,235 | B2 | 8/2006 | Francischelli |
| 7,155,293 | B2 | 12/2006 | Westlund et al. |
| 7,189,231 | B2 | 3/2007 | Clague et al. |
| 7,214,234 | B2 | 5/2007 | Rapacki et al. |
| 7,231,260 | B2 | 6/2007 | Wallace et al. |
| 7,250,051 | B2 | 7/2007 | Francischelli |
| 7,288,075 | B2 | 10/2007 | Parihar et al. |
| 7,303,554 | B2 | 12/2007 | LaLonde et al. |
| 7,306,598 | B2 | 12/2007 | Truckai et al. |
| 7,335,198 | B2 | 2/2008 | Eggers et al. |
| 7,341,063 | B2 | 3/2008 | Garbibaldi et al. |
| 7,367,341 | B2 | 5/2008 | Anderson et al. |
| 7,374,567 | B2 | 5/2008 | Heuser |
| 7,387,636 | B2 * | 6/2008 | Cohn ............... A61B 17/11 606/167 |
| 7,407,506 | B2 | 8/2008 | Makower |
| 7,628,768 | B2 | 12/2009 | Faul et al. |
| 7,702,387 | B2 | 4/2010 | Stevenson et al. |
| 7,727,268 | B2 | 6/2010 | Cunniffe et al. |
| 7,744,596 | B2 | 6/2010 | Young et al. |
| 7,811,281 | B1 | 10/2010 | Rentrop |
| 7,828,814 | B2 | 11/2010 | Brenneman et al. |
| 7,846,172 | B2 | 12/2010 | Makower |
| 7,849,860 | B2 | 12/2010 | Makower et al. |
| 7,857,809 | B2 | 12/2010 | Drysen |
| 7,881,797 | B2 | 2/2011 | Griffin et al. |
| 7,955,326 | B2 | 6/2011 | Paul et al. |
| 7,967,769 | B2 | 6/2011 | Faul et al. |
| 7,967,770 | B2 | 6/2011 | Li et al. |
| 8,010,208 | B2 | 8/2011 | Nimer et al. |
| 8,048,016 | B2 | 11/2011 | Faul et al. |
| 8,052,680 | B2 | 11/2011 | Hassett et al. |
| 8,062,321 | B2 | 11/2011 | Heuser et al. |
| RE43,007 | E | 12/2011 | LaLonde et al. |
| 8,075,555 | B2 | 12/2011 | Truckai et al. |
| 8,088,171 | B2 | 1/2012 | Brenneman |
| 8,100,899 | B2 | 1/2012 | Doty et al. |
| 8,118,809 | B2 | 2/2012 | Paul et al. |
| 8,135,467 | B2 | 3/2012 | Markowitz et al. |
| 8,142,454 | B2 | 3/2012 | Harrison et al. |
| 8,192,425 | B2 | 6/2012 | Mirza et al. |
| 8,200,466 | B2 * | 6/2012 | Spilker ............... G06F 19/3437 703/11 |
| 8,226,592 | B2 | 7/2012 | Brenneman et al. |
| 8,231,618 | B2 | 7/2012 | Viswanathan et al. |
| 8,236,014 | B2 | 8/2012 | Brenneman et al. |
| 8,262,649 | B2 | 9/2012 | Francischelli |
| 8,273,095 | B2 | 9/2012 | Brenneman et al. |
| 8,333,758 | B2 | 12/2012 | Joye et al. |
| 8,361,061 | B2 | 1/2013 | Esch et al. |
| 8,366,707 | B2 | 2/2013 | Kassab et al. |
| 8,382,697 | B2 * | 2/2013 | Brenneman ............ A61B 17/11 604/9 |
| 8,409,196 | B2 | 4/2013 | Durgin et al. |
| 8,413,664 | B2 | 4/2013 | Appling |
| 8,414,572 | B2 | 4/2013 | Davison et al. |
| 8,419,681 | B2 | 4/2013 | Sell |
| 8,439,909 | B2 | 5/2013 | Wang et al. |
| 8,454,587 | B2 | 6/2013 | LaLonde et al. |
| 8,475,441 | B2 | 7/2013 | Babkin et al. |
| 8,486,062 | B2 | 7/2013 | Belhe et al. |
| 8,486,064 | B2 | 7/2013 | Van Wyk et al. |
| 8,551,032 | B2 | 10/2013 | Faul et al. |
| 8,574,185 | B2 | 11/2013 | Faul et al. |
| 8,585,700 | B2 | 11/2013 | Katou |
| 8,608,754 | B2 | 12/2013 | Wensel et al. |
| 8,641,724 | B2 | 2/2014 | Brenneman et al. |
| 8,649,879 | B2 | 2/2014 | DiGiore et al. |
| 8,676,309 | B2 | 3/2014 | Deem et al. |

(56) References Cited

U.S. PATENT DOCUMENTS

| | | |
|---|---|---|
| 8,685,014 B2 | 4/2014 | Babkin et al. |
| 8,700,179 B2 | 4/2014 | Pianca et al. |
| 8,715,281 B2 | 5/2014 | Barlow et al. |
| 8,758,334 B2 | 6/2014 | Coe et al. |
| 8,784,409 B2 | 6/2014 | Robilotto et al. |
| 8,771,267 B2 | 7/2014 | Kunis et al. |
| 8,790,341 B2 | 7/2014 | Pappone et al. |
| 8,876,699 B2 | 11/2014 | Sato et al. |
| 8,876,815 B2 | 11/2014 | Coe et al. |
| 8,882,765 B2 | 11/2014 | Kassab et al. |
| 8,911,435 B2 | 12/2014 | Katoh et al. |
| 8,951,251 B2 | 2/2015 | Willard |
| 9,017,323 B2 | 4/2015 | Miller et al. |
| 9,039,702 B2 | 5/2015 | Miller et al. |
| 9,072,880 B2 | 7/2015 | Phillips et al. |
| 9,089,316 B2 | 7/2015 | Baust et al. |
| 9,155,827 B2 | 10/2015 | Franano |
| 9,204,916 B2 | 12/2015 | Lalonde |
| 9,283,034 B2 | 3/2016 | Katoh et al. |
| 9,364,280 B2 | 6/2016 | Zarins et al. |
| 9,402,560 B2 | 8/2016 | Organ et al. |
| 9,414,885 B2 | 8/2016 | Willard |
| 9,439,728 B2 | 9/2016 | Hull et al. |
| 9,445,868 B2 | 9/2016 | Hull et al. |
| 9,452,015 B2 | 9/2016 | Kellerman et al. |
| 9,486,276 B2 | 11/2016 | Rios et al. |
| 9,782,533 B2 * | 10/2017 | Brenneman ......... A61M 1/3655 |
| 2001/0029384 A1 | 10/2001 | Nicholas et al. |
| 2002/0072739 A1 | 6/2002 | Lee et al. |
| 2002/0113678 A1 | 8/2002 | Creighton |
| 2002/0151945 A1 | 10/2002 | Gobin et al. |
| 2003/0009163 A1 | 1/2003 | Messing et al. |
| 2003/0220674 A1 | 11/2003 | Anderson et al. |
| 2004/0059211 A1 | 3/2004 | Patel et al. |
| 2004/0059280 A1 | 3/2004 | Makower et al. |
| 2004/0167506 A1 | 8/2004 | Chen |
| 2004/0215220 A1 | 10/2004 | Dolan et al. |
| 2004/0236360 A1 | 11/2004 | Cohn et al. |
| 2005/0033401 A1 | 2/2005 | Cunniffe et al. |
| 2005/0065509 A1 | 3/2005 | Coldwell et al. |
| 2005/0245925 A1 | 11/2005 | Iki et al. |
| 2005/0251120 A1 | 11/2005 | Anderson et al. |
| 2006/0079897 A1 | 4/2006 | Harrison et al. |
| 2006/0111704 A1 * | 5/2006 | Brenneman ............ A61B 17/11 606/41 |
| 2007/0173878 A1 | 7/2007 | Heuser |
| 2007/0203515 A1 | 8/2007 | Heuser et al. |
| 2008/0021532 A1 | 1/2008 | Kveen et al. |
| 2008/0051626 A1 | 2/2008 | Sato et al. |
| 2008/0065019 A1 | 3/2008 | Heuser et al. |
| 2008/0091192 A1 | 4/2008 | Paul et al. |
| 2008/0119879 A1 * | 5/2008 | Brenneman ............ A61B 17/11 606/153 |
| 2008/0140061 A1 | 6/2008 | Toubia et al. |
| 2008/0171944 A1 | 7/2008 | Brenneman et al. |
| 2008/0183164 A1 | 7/2008 | Elkins et al. |
| 2008/0188848 A1 | 8/2008 | Deutmeyer et al. |
| 2008/0275442 A1 | 11/2008 | Paul et al. |
| 2009/0036872 A1 | 2/2009 | Fitzgerald et al. |
| 2009/0076324 A1 | 3/2009 | Takayama et al. |
| 2009/0112119 A1 | 4/2009 | Kim |
| 2009/0118722 A1 | 5/2009 | Ebbers et al. |
| 2009/0124847 A1 | 5/2009 | Doty et al. |
| 2009/0198232 A1 | 8/2009 | Young et al. |
| 2009/0248148 A1 | 10/2009 | Shaolian et al. |
| 2009/0275876 A1 | 11/2009 | Brenneman et al. |
| 2009/0281379 A1 | 11/2009 | Binmoeller et al. |
| 2009/0318849 A1 | 12/2009 | Hobbs et al. |
| 2010/0004623 A1 | 1/2010 | Hamilton, Jr. et al. |
| 2010/0010488 A1 | 1/2010 | Kassab et al. |
| 2010/0082058 A1 | 4/2010 | Kassab |
| 2010/0130835 A1 | 5/2010 | Brenneman et al. |
| 2010/0198206 A1 | 8/2010 | Levin |
| 2010/0204691 A1 | 8/2010 | Bencini |
| 2010/0222664 A1 | 9/2010 | Lemon et al. |
| 2010/0256616 A1 | 10/2010 | Katoh et al. |
| 2010/0280316 A1 | 11/2010 | Deitz et al. |
| 2010/0280514 A1 | 11/2010 | Zerfas et al. |
| 2010/0286705 A1 | 11/2010 | Vassiliades, Jr. |
| 2010/0292685 A1 | 11/2010 | Katoh et al. |
| 2010/0298645 A1 | 11/2010 | Deutch |
| 2011/0015657 A1 | 1/2011 | Brenneman et al. |
| 2011/0112427 A1 | 5/2011 | Phillips et al. |
| 2011/0118735 A1 | 5/2011 | Abou-Marie et al. |
| 2011/0201990 A1 | 8/2011 | Franano |
| 2011/0213309 A1 | 9/2011 | Young et al. |
| 2011/0218476 A1 | 9/2011 | Kraemer et al. |
| 2011/0270149 A1 | 11/2011 | Faul et al. |
| 2011/0288392 A1 | 11/2011 | de la Rama et al. |
| 2011/0288544 A1 | 11/2011 | Verin et al. |
| 2011/0306959 A1 | 12/2011 | Kellerman et al. |
| 2011/0306993 A1 | 12/2011 | Hull et al. |
| 2011/0319976 A1 * | 12/2011 | Iyer ........................ A61F 2/064 623/1.11 |
| 2012/0010556 A1 | 1/2012 | Faul et al. |
| 2012/0022518 A1 | 1/2012 | Levinson |
| 2012/0035539 A1 | 2/2012 | Tegg |
| 2012/0046678 A1 | 2/2012 | LeMaitre et al. |
| 2012/0059398 A1 | 3/2012 | Pate et al. |
| 2012/0065652 A1 | 3/2012 | Cully et al. |
| 2012/0078342 A1 | 3/2012 | Vollkron et al. |
| 2012/0089123 A1 | 4/2012 | Organ et al. |
| 2012/0101423 A1 | 4/2012 | Brenneman et al. |
| 2012/0116354 A1 | 5/2012 | Heuser |
| 2012/0157992 A1 | 6/2012 | Smith et al. |
| 2012/0209377 A1 | 8/2012 | Machold et al. |
| 2012/0215088 A1 | 8/2012 | Wang et al. |
| 2012/0239021 A1 | 9/2012 | Doty et al. |
| 2012/0277736 A1 | 11/2012 | Francischelli |
| 2012/0281330 A1 | 11/2012 | Abbott et al. |
| 2012/0289953 A1 | 11/2012 | Berzak et al. |
| 2012/0296262 A1 | 11/2012 | Ogata et al. |
| 2012/0302935 A1 * | 11/2012 | Miller ............ A61B 17/320725 604/8 |
| 2013/0041306 A1 * | 2/2013 | Faul ........................ A61B 17/11 604/8 |
| 2013/0056876 A1 | 5/2013 | Harvey et al. |
| 2013/0110105 A1 | 5/2013 | Vankov |
| 2013/0172881 A1 | 7/2013 | Hill et al. |
| 2013/0190744 A1 | 7/2013 | Avram et al. |
| 2013/0190754 A1 | 7/2013 | Paul et al. |
| 2013/0216351 A1 | 8/2013 | Griffin |
| 2013/0226170 A1 | 8/2013 | Seddon et al. |
| 2013/0261368 A1 | 10/2013 | Schwartz |
| 2013/0282000 A1 | 10/2013 | Parsonage |
| 2014/0031674 A1 | 1/2014 | Newman et al. |
| 2014/0094791 A1 | 4/2014 | Hull et al. |
| 2014/0100557 A1 | 4/2014 | Bohner et al. |
| 2014/0100562 A1 | 4/2014 | Sutermeister et al. |
| 2014/0107642 A1 | 4/2014 | Rios et al. |
| 2014/0166098 A1 | 6/2014 | Kian et al. |
| 2014/0188028 A1 | 7/2014 | Brenneman et al. |
| 2014/0276335 A1 | 9/2014 | Pate |
| 2015/0005759 A1 | 1/2015 | Welches et al. |
| 2015/0011909 A1 | 1/2015 | Holmin et al. |
| 2015/0018810 A1 | 1/2015 | Baust et al. |
| 2015/0057654 A1 | 2/2015 | Leung et al. |
| 2015/0057687 A1 | 2/2015 | Gittard et al. |
| 2015/0094645 A1 | 4/2015 | Omar-Pasha |
| 2015/0112195 A1 | 4/2015 | Berger et al. |
| 2015/0134055 A1 | 5/2015 | Spence et al. |
| 2015/0141836 A1 | 5/2015 | Naumann et al. |
| 2015/0164573 A1 | 6/2015 | Delaney |
| 2015/0196356 A1 | 7/2015 | Kauphusman et al. |
| 2015/0196360 A1 | 7/2015 | Grantham et al. |
| 2015/0201962 A1 | 7/2015 | Kellerman et al. |
| 2015/0258308 A1 | 9/2015 | Pate |
| 2015/0080886 A1 | 11/2015 | Miller et al. |
| 2015/0313668 A1 | 11/2015 | Miller et al. |
| 2015/0320472 A1 | 11/2015 | Ghaffari et al. |
| 2016/0022345 A1 | 1/2016 | Baust et al. |
| 2016/0058452 A1 * | 3/2016 | Brenneman ............ A61B 17/11 606/153 |
| 2016/0058956 A1 | 3/2016 | Cohn et al. |

(56) References Cited

U.S. PATENT DOCUMENTS

| | | | |
|---|---|---|---|
| 2016/0067449 | A1 | 3/2016 | Misener et al. |
| 2016/0082234 | A1 | 3/2016 | Schwartz et al. |
| 2016/0128855 | A1 | 5/2016 | Heuser et al. |
| 2016/0135881 | A1 | 5/2016 | Katoh et al. |
| 2016/0184011 | A1 | 6/2016 | Krishnan |
| 2016/0206317 | A1 | 7/2016 | Dickinson et al. |
| 2017/0119464 | A1 | 5/2017 | Rios et al. |
| 2017/0172679 | A1 | 6/2017 | Doty et al. |
| 2017/0202603 | A1 | 7/2017 | Cohn et al. |
| 2017/0202616 | A1 | 7/2017 | Pate et al. |
| 2018/0116522 | A1 | 5/2018 | Brenneman et al. |

FOREIGN PATENT DOCUMENTS

| | | |
|---|---|---|
| CN | 101730557 A | 6/2010 |
| EP | 0 889 705 A1 | 1/1999 |
| EP | 1983907 B1 | 10/2008 |
| JP | 11-512640 A | 11/1999 |
| JP | 2000-511787 | 9/2000 |
| JP | 2004-501720 A | 1/2004 |
| JP | 3493464 B2 | 2/2004 |
| JP | 2004-514467 | 5/2004 |
| JP | 2003-181370 | 7/2006 |
| RU | 2168951 C1 | 6/2001 |
| WO | WO-97/13463 A1 | 4/1997 |
| WO | WO-97/32532 | 9/1997 |
| WO | WO-97/33522 A1 | 9/1997 |
| WO | WO 99/56640 A1 | 11/1999 |
| WO | WO-02/02163 A2 | 1/2002 |
| WO | WO-02/02163 A3 | 1/2002 |
| WO | WO 2002/003893 A2 | 1/2002 |
| WO | 2008010039 A2 | 1/2008 |
| WO | WO-2009/005644 A2 | 1/2009 |
| WO | WO-2009/005644 A3 | 1/2009 |
| WO | WO-2011/100625 A2 | 8/2011 |
| WO | WO-2011/100625 A3 | 8/2011 |
| WO | WO-2012/068273 A1 | 5/2012 |
| WO | 2013112584 A1 | 8/2013 |
| WO | WO-2014/052919 A1 | 4/2014 |
| WO | WO-2014/059351 A1 | 4/2014 |
| WO | WO-2014/137830 A1 | 9/2014 |
| WO | WO-2014/153229 A1 | 9/2014 |
| WO | WO-2015/040557 A1 | 3/2015 |
| WO | WO-2015/061614 A1 | 4/2015 |
| WO | WO-2015/085119 A1 | 6/2015 |
| WO | 2015108984 A1 | 7/2015 |
| WO | WO-2015/138998 A1 | 9/2015 |
| WO | WO-2016/033374 | 3/2016 |
| WO | WO-2016/033380 | 3/2016 |
| WO | WO-2017/124059 | 7/2017 |
| WO | WO-2017/124060 | 7/2017 |
| WO | WO-2017/124062 | 7/2017 |
| WO | WO-2018/057095 | 3/2018 |

OTHER PUBLICATIONS

Banasik et al. (2011). "A rare variant route of the ulnar artery does not contraindicate the creation of a fistula in the wrist of a diabetic patient with end-stage renal disease," *Postepy Hig Med Dosw.* 65:654-657.

Bharat et al. (2012). "A novel technique of vascular anastomosis to prevent juxta-anastomotic stenosis following arteriovenous fistula creation," *J. Vascular Surgery* 55(1):274-280.

Bode et al. (2011). "Clinical study protocol for the arch project Computational modeling for improvement of outcome after vascular access creation," *J. Vasc. Access* 12(4):369-376.

Davidson, I. et al. (2008). "Duplex Ultrasound Evaluation for Dialysis Access Selection and Maintenance: A Practical Guide," *The Journal of Vascular Access* 9(1):1-9.

Extended European Search Report dated Oct. 19, 2016, for EP Application No. 14 770 396.1, filed on Mar. 14, 2014, 7 pages.

Final Office Action dated Mar. 10, 2016, for U.S. Appl. No. 14/052,477, filed Oct. 11, 2013, 11 pages.

Final Office Action dated Oct. 6, 2016, for U.S. Appl. No. 14/697,451, filed Apr. 27, 2015, 11 pages.

Gracz, et al. (1977). "Proximal forearm fistula for maintenance hemodialysis," *Kidney International* 11:71-75.

International Search Report and Written Opinion dated Feb. 23, 2012, for PCT Patent Application No. PCT/US2011/061026, filed on Nov. 16, 2011, 8 pages.

International Search Report and Written Opinion dated Jan. 10, 2014, for PCT Patent Application No. PCT/US2013/064657, filed on Oct. 11, 2013, 8 pages.

International Search Report and Written Opinion dated Aug. 22, 2014, for PCT Patent Application No. PCT/US2014/029731, filed on Mar. 14, 2014, 11 pages.

International Search Report and Written Opinion dated Jun. 17, 2015, for PCT Patent Application No. PCT/US2015/020604, filed on Mar. 13, 2015, 8 pages.

Jennings, W.C. et al. (2011). "Primary arteriovenous fistula inflow proximalization for patients at high risk for dialysis access-associated ischemic steal syndrome," *J. Vasc. Surgery* 54(2):554-558.

Kinnaert, et al. (1971). "Ulnar Arteriovenous Fistula for Maintenance Haemodialysis," *British J. Surgery* 58(9):641-643.

Morale et al. (2011). "Venae comitantes as a potential vascular resource to create native arteriovenous fistulae," *J. Vasc. Access* 12(3):211-214.

Non-Final Office Action dated May 2, 2016, for U.S. Appl. No. 14/697,451, filed Apr. 27, 2015, 12 pages.

Non-Final Office Action dated Aug. 8, 2014, for U.S. Appl. No. 13/298,169, filed Nov. 16, 2011, 15 pages.

Non-Final Office Action dated Jul. 29, 2015, for U.S. Appl. No. 14/052,477, filed Oct. 11, 2013, 15 pages.

Notice of Allowance dated Dec. 31, 2014, for U.S. Appl. No. 13/298,169, filed Nov. 16, 2011, 10 pages.

Notice of Allowance dated Mar. 11, 2015, for U.S. Appl. No. 13/298,169, filed Nov. 16, 2011, 4 pages.

Notice of Allowance dated Jan. 23, 2015, for U.S. Appl. No. 14/550,747, filed Nov. 21, 2014, 10 pages.

Notice of Allowance dated Jul. 12, 2016, for U.S. Appl. No. 14/052,477, filed Oct. 11, 2013, 7 pages.

Shenoy, S. (2009). "Surgical anatomy of upper arm: what is needed for AVF planning," *The Journal of Vascular Access* 10:223-232.

Vachharajani, T. (2010). "Atlas of Dialysis Vascular Access," Wake Forest University School of Medicine, 77 total pages.

Whittaker et al. (2011). "Prevention better than cure. Avoiding steal syndrome with proximal radial or ulnar arteriovenous fistulae," *J. Vasc. Access* 12(4):318-320.

International Search Report and Written Opinion dated Mar. 31, 2017, for PCT Patent Application No. PCT/US17/13611, filed on Jan. 15, 2017, 10 pages.

Non-Final Office Action dated Apr. 13, 2017, for U.S. Appl. No. 14/697,451, filed Apr. 27, 2015, 14 pages.

Invitation to Pay Additional Fees and, Where Applicable, Protest Fee dated Mar. 31, 2017, for PCT Application No. PCT/US17/13613, filed Jan. 15, 2017, 3 pages.

International Search Report and Written Opinion dated Jun. 1, 2017, for PCT Patent Application No. PCT/US2017/13613, filed Jan. 15, 2017, 18 pages.

Non-Final Office Action dated Jul. 10, 2017, for U.S. Appl. No. 14/214,503, filed Mar. 14, 2014, 11 pages.

International Search Report and Written Opinion dated Jan. 6, 2016, from the International Searching Authority for Application No. PCTUS2015047274, filed Aug. 27, 2015, 12 pages.

Invitation to Pay Additional Fees and, where Applicable, Protest Fee issued by the International Searching Authority for Application No. PCTUS2015047274, filed Aug. 27, 2015, dated Oct. 22, 2015, 2 pages.

International Search Report and Written Opinion dated May 19, 2017, by the International Searching Authority for Application No. PCT/US2017/013610, filed Jan. 15, 2017, 10 pages.

International Search Report and Written Opinion dated Sep. 28, 2017, by the International Searching Authority for Application No. PCT/US2017/042937, filed Jul. 19, 2017, 11, pages.

(56) References Cited

OTHER PUBLICATIONS

Extended European Search Report dated Oct. 16, 2017, for EP Application No. 11841243.6, filed Nov. 16, 2011, 6 pages.
Non-Final Office Action issued by the United States Patent and Trademark Office for U.S. Appl. No. 14/657,997, dated Oct. 18, 2017, 10 pages.
Maybury et al., "The Effect of Roll Angle on the Performance of Halbach Arrays," University of California—San Diego, Center for Magnetic Recording Research (2008), 19 pages.
Non-Final Office Action issued by The United States Patent and Trademark Office for U.S. Appl. No. 14/214,503, dated Mar. 19, 2018, 16 pages.
Non-Final Office issued by The United States Patent and Trademark Office for U.S. Appl. No. 14/838,225, dated Apr. 23, 2018, 11 pages.
Notice of Allowance issued by The United States Patent and Trademark Office for U.S. Appl. No. 14/697,451, dated Apr. 13, 2018, 13 pages.
Final Office Action issued by The United States Patent and Trademark Office for U.S. Appl. No. 14/657,997, dated Jun. 22, 2018, 12 pages.
Extended European Search Report for EP Application No. 17739123.2.
Choi, et al., Design of a Halbach Magnet Array Based on Optimization Techniques; IEEE Transactions on Magnetics, vol. 44, No. 10, Oct. 2008, pp. 2361-2366. (Year: 2008).

* cited by examiner

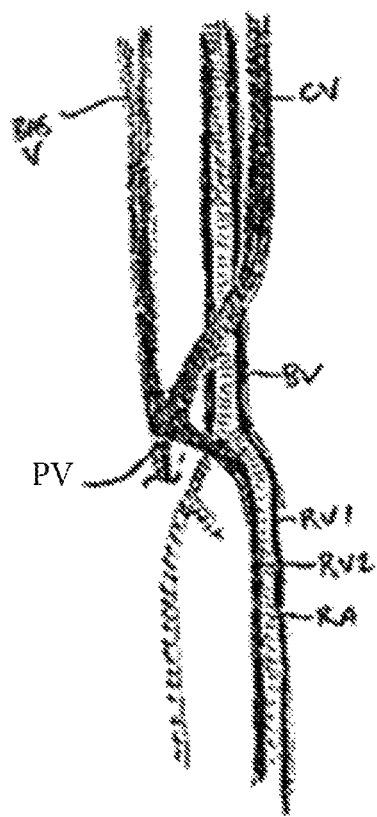
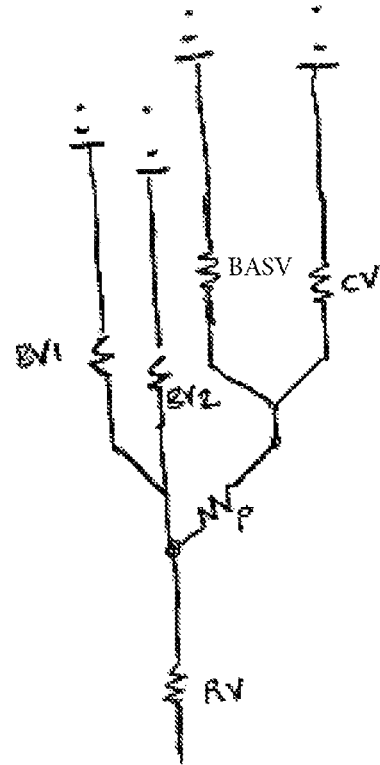
FIG. 4C                    FIG. 4D

METHODS FOR TREATING HYPERTENSION AND REDUCING BLOOD PRESSURE WITH FORMATION OF FISTULA

CROSS-REFERENCE TO RELATED APPLICATIONS

This application claims priority to U.S. Provisional Application Ser. No. 62/114,040, filed on Feb. 9, 2015, and titled "METHODS FOR TREATING HYPERTENSION," the content of which is hereby incorporated by reference in its entirety.

FIELD

The current invention relates to methods for forming a fistula between two blood vessels to reduce blood pressure.

BACKGROUND

Blood pressure is a reflection of the amount of blood that the heart pumps and the amount of flow resistance to blood flow in the arteries. Hypertension, or high blood pressure, is a medical condition of elevated blood pressure in the arteries. In some cases, hypertension develops gradually over many years due to a variety of factors (e.g., genetics and diet), while in other cases, hypertension is caused by an underlying condition such as kidney problems, thyroid problems, or certain medications. When uncontrolled, hypertension can lead to serious health problems such as heart disease, heart attack, and stroke.

In patients diagnosed with high systemic or pulmonary blood pressure (hypertension), reduction of blood pressure may reduce risk of stroke, aneurysm, kidney, cardiovascular, pulmonary, and peripheral vascular disease. In 2012, the prevalence of hypertension in the U.S. among adults older than 18 years of age was 30%. Utilization of antihypertensive medication to treat moderately high blood pressure is widespread. However, this may have limited efficacy because of high costs, undesirable side effects, and/or the need for continued patient compliance. Certain patients may remain unresponsive to this therapy or develop resistance to treatments leaving their blood pressure uncontrolled. It may therefore be useful to find alternative treatments for hypertension.

BRIEF SUMMARY

Described here are methods for treating hypertension in a patient in need thereof. In general, the methods comprise treating a patient having hypertension comprising advancing a first catheter into a first blood vessel of the patient. The first catheter may comprise an electrode. A fistula may be formed between the first blood vessel and a second blood vessel to reduce a blood pressure of the patient.

In some variations, a method of treating a patient having hypertension may comprise determining a desired amount of blood pressure reduction. The fistula may be configured to reduce blood pressure by about at least 15%. The patient may have a systolic blood pressure of more than about 150 mmHG. The hypertension may be drug resistant hypertension. The first blood vessel and the second blood vessel may be selected based on the desired amount of blood pressure reduction. A fistula characteristic may be selected based on the desired amount of blood pressure reduction. The fistula characteristic may comprise one or more of fistula size, number of fistulas, spacing between the fistulas, and fistula arrangement. The fistula arrangement may comprise a series of fistulas located axially along the blood vessels.

The methods may include additional variations. In some variations, one or more of the blood vessels may be modified. Modifying one or more of the blood vessels may comprise one or more of shrinking one or more of the blood vessels proximal to the fistula, shrinking a fistula site prior to forming the fistula, inserting a stent proximal to the fistula in one or more of the first blood vessel and the second blood vessel, and occluding the fistula.

Also described here are methods for treating a patient having hypertension comprising advancing a first catheter into a first deep vein and a second catheter into an artery. The first catheter may comprise an electrode. A first fistula may be formed between the first deep vein and the artery with the electrode to reduce a blood pressure of the patient.

In some variations, a desired amount of blood pressure reduction is determined and the fistula(s) may be formed based on the desired amount of blood pressure reduction. In some variations, the artery may be a proximal ulnar artery and the first deep vein may be a deep ulnar vein. In other variations, the artery may be a radial artery and the first deep vein may be a radial vein. A second fistula may be formed between the artery and a second deep vein.

Also described here are methods for treating a patient having hypertension comprising advancing a first catheter into a first deep vein and a second catheter into an artery. The first catheter may comprise an electrode. A fistula may be formed between the first deep vein and the artery with the electrode. The fistula may be configured to reduce blood pressure of the patient below a desired blood pressure. One or more of the first deep vein and the artery may be modified to increase the blood pressure to the desired blood pressure.

BRIEF DESCRIPTION

FIGS. 4A-4E depict illustrative vascular anatomy and corresponding lumped parameter models.

DETAILED DESCRIPTION

A fistula is generally a passageway formed between two internal organs. Generally described here are methods for treating a patient having hypertension by forming one or more fistulas between blood vessels of the arm to reduce blood pressure. Forming a fistula between two blood vessels may have one or more beneficial functions. The methods described herein may not only reduce localized, peripheral vascular resistance, but may also reduce overall systemic arterial blood pressure. Blood flow encounters resistance from the systemic vasculature, which is referred to as systemic vascular resistance (SVR). SVR excludes resistance from the pulmonary vasculature. SVR is used in calculations of blood pressure, blood flow and cardiac function. A fistula formed between an artery and vein redirects blood from the arterial system to the venous system, thus bypassing peripheral circulation and decreasing SVR. For example, the formation of one or more fistulas between an artery and one or more veins in the arm may increase arterial inflow and may be sufficient to have a beneficial clinical treatment effect. Furthermore, it is advantageous for such an appreciable reduction in blood pressure to be achieved by a minimally invasive, lower risk treatment at a peripheral location. Thus, intervention by fistula formation at a peripheral location may provide an improved method of treatment for hypertension. Moreover, the methods described herein may titrate blood flow to produce a desired reduction in blood pressure suited to each patient.

Figure 1:
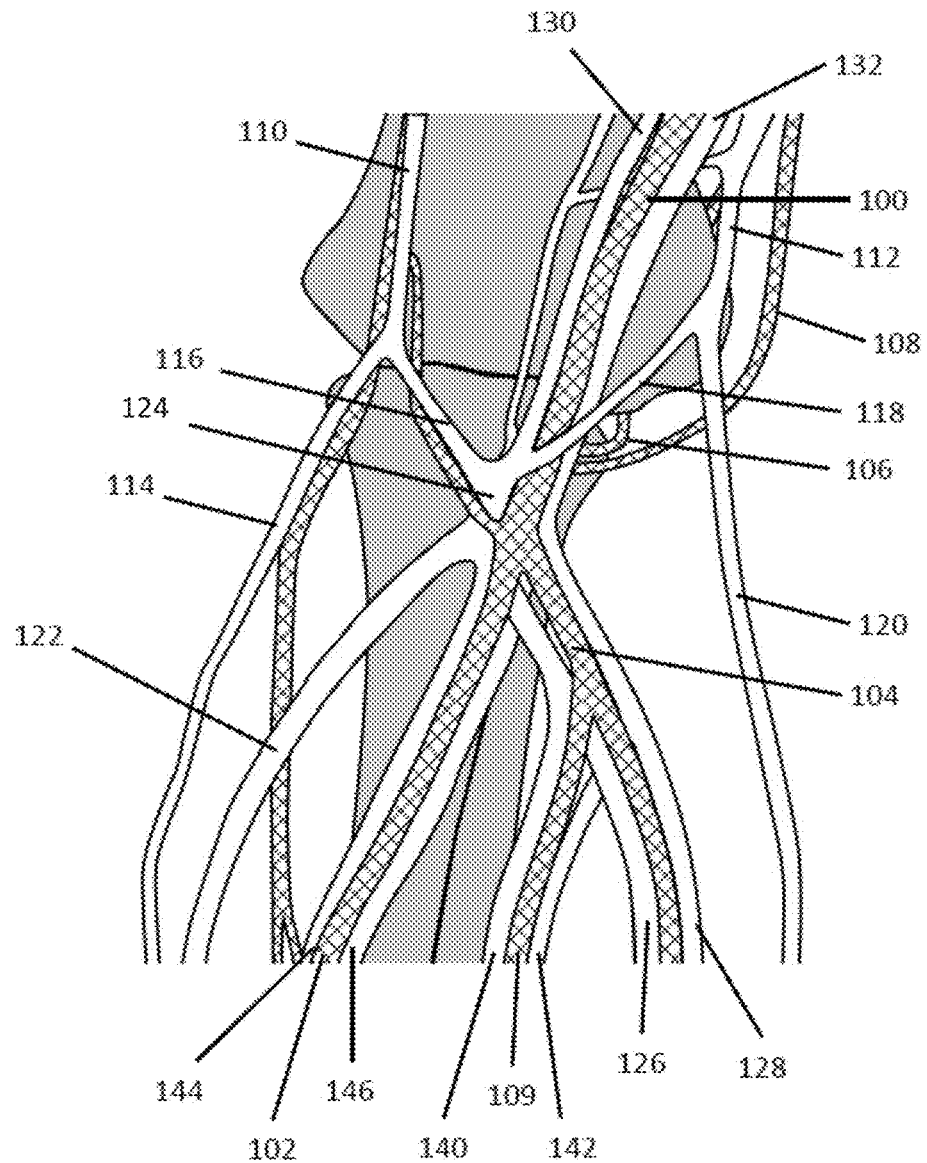
FIG. 1 is an illustrative depiction of the vascular anatomy of the arm.

In instances where the arm is the relevant anatomy, it may be helpful to briefly identify and describe the anatomy of the arm around the elbow. FIG. 1 shows an anterior view of the right arm as would be seen with the palm facing upward. As shown there, the brachial artery (100) extends superficially and distally from the upper arm and sinks deeply into the arm near the elbow joint, where the brachial artery (100) branches into the radial artery (102) and the ulnar artery (104). The upper portion of the ulnar artery (104) is deeply seated within the arm beneath the superficial flexor muscles (not shown), and leads down the ulnar side of the forearm to the wrist. The anterior ulnar recurrent artery (106) and the posterior ulnar recurrent artery (108) branch off of the ulnar artery (104) just below the elbow joint, and these arteries supply blood to the joint and surrounding muscles. Further down the arm (typically just below the radial tuberosity of the radius bone (not shown)), the interosseous artery (109) branches off from the ulnar artery (104) and eventually feeds into the posterior and anterior interosseous arteries.

Also shown in FIG. 1 are the cephalic vein and the basilic vein. The cephalic vein runs along the outer border of the bicep muscle (not shown) and continues down into the forearm. The cephalic vein of the upper arm is labeled in FIG. 1 as cephalic vein (110), while the cephalic vein of the lower arm is labeled as cephalic vein (114). The median cephalic vein (116) joins the cephalic vein (110)/(114) near the elbow joint. The basilic vein runs along the inner side of the bicep muscle and continues into the forearm (the basilic vein of the upper arm is labeled as basilic vein (112), while the basilic vein of the lower arm is labeled as common ulnar vein (120)). The median cubital vein (118) (in some instances referred to as the median basilic vein) joins the basilic vein (112) and the common ulnar vein (120) (in some instances, this vein segment is also referred to as the basilic vein of the forearm or forearm basilic vein). The median cubital vein (118) and the median cephalic vein (116) are formed at the branching of the median antebrachial vein (122) (also known as the median vein). Near the branching of the median vein (122) into the median cubital vein (118) and the medial cephalic vein (116), a perforating branch (124) connects these vessels with the deep veins of the arm through the antebrachial fascia (not shown). As shown in FIG. 1, perforating branch (124) communicates with a first deep ulnar vein (126) and a second deep ulnar vein (128). These deep ulnar veins may run substantially parallel on either side of the ulnar artery (104) between the brachial artery (100) and the interosseous artery (109), and may branch away from ulnar artery (104) distal to the interosseous artery (109). Between the brachial artery (100) and the interosseous artery (109), the deep ulnar veins are typically located in close proximity to the ulnar artery, and usually less than 2 mm separate the ulnar artery from the deep ulnar veins. Along the length of the deep ulnar veins, transverse branches (not shown) may occasionally connect the deep ulnar veins. Also shown in FIG. 1 are first (130) and second (132) brachial veins. The brachial veins generally run along the brachial artery (100), and the deep ulnar veins feed into the brachial veins near the elbow joint. Additionally, a pair of radial veins ((144) and (146)) may run along the radial artery, and may feed into one or both of the brachial veins. Also shown in FIG. 1 are first (140) and second (142) interosseous veins, which may branch off from the first (126) and second (128) deep ulnar veins respectively, and which may run substantially parallel to the interosseous artery (109).

I. Devices

Figure 2:
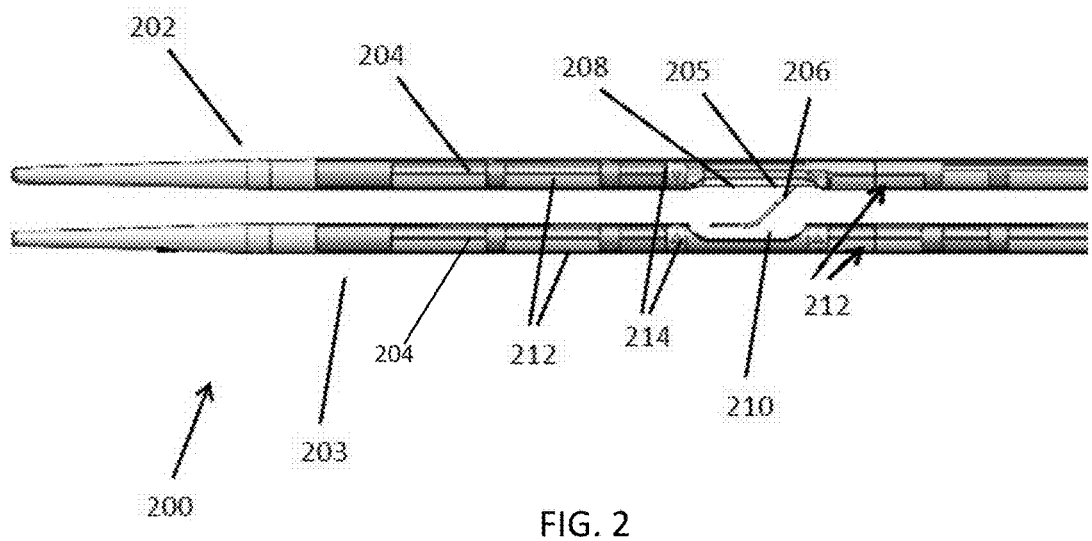
FIG. 2 is a side view of a variation of a catheter system suitable for use with the methods described here.

Generally described here are catheters for treating hypertension. FIG. 2 depicts one illustrative variation of a catheter system (200) that may be used to form a fistula between an artery (e.g., ulnar artery or radial artery) and a vein (e.g., deep ulnar vein or radial vein). As shown there, system (200) may comprise a first catheter (202) and a second catheter (203). The first catheter (202) may comprise a catheter body (204) and an electrode (206) which may be advanced out of an opening (205) in the catheter body (204). Current may be passed through the electrode (206) to ablate or otherwise remove tissue contacted by the electrode (206). The size and/or shape of the electrode (206) may at least in part determine the size (e.g., length, width) and/or shape of the fistula formed by the ablation. For example, the size and/or shape of the electrode (206) may be selected to result in a fistula with a particular configuration, which may in turn be based on the desired effect on systolic and/or diastolic blood pressure. For example, one variation of a first catheter (202) may include an electrode (206) of a first length, while another variation of a first catheter (202) may include an electrode (206) of a second length that is different from the first length. Accordingly, different electrodes (206) may be used to create fistulas of different sizes and/or shapes in a single patient, so as to customize or optimize the method of reducing blood pressure in the patient. Alternatively, other variations of a catheter may include one or more electrodes of varying sizes and shapes to form different fistulas.

In some variations, the first catheter (202) may comprise an insulating housing (208) (e.g., a ceramic housing or the like) within the catheter body, which may help protect other components of the first catheter (202) from heat that may be generated by the electrode (206) during tissue removal. In some variations, the electrode (206) may be selectively moved from a position in which the electrode (206) is retained or otherwise held in the catheter body (204) to a position in which the electrode (206) extends away from the catheter body (204) (such as shown in FIG. 2), and electrode (206) may also be selectively moved back to a retracted/low-profile position (either the same or a different position as the previous retracted position) following ablation of tissue. In some variations, the electrode (206) may be biased toward an extended position when not otherwise restrained by the catheter body (204). In some variations, the electrode may be configured such that it is biased to move from a position in which the electrode is flush with the catheter body to a configuration in which the electrode extends away from the catheter when the electrode is unrestrained by tissue. In some variations, one or more portions of the catheter body (204) may be energized to provide heating to fluid or tissue in contact with and/or surrounding the catheter body (204).

In some variations, the second catheter (203) may comprise a catheter body (204) and a recess (210) for receiving an electrode (206) of the first catheter (202) as the electrode (206) cuts through tissue and extends away from the first catheter (202). In some variations, a backstop may be provided in place of recess (210) to compress against tissue to reduce a thickness of tissue for cutting by the electrode (206). Additionally or alternatively, the second catheter (203) may include an electrode for forming a fistula. An electrode of a second catheter (203) may include an insulating housing (not shown) within the catheter body, which may help protect other components of the second catheter (203) from heat that may be generated by an electrode during tissue removal. An electrode of the second catheter (203) may be similar to an electrode (206) discussed above with respect to the first catheter. For instance, an electrode of the catheter may comprise an extended position and a retracted/low-profile position. In some variations, one or more portions of the catheter body (204) may be energized to provide heating to fluid or tissue in contact with or surrounding the catheter body (204).

The methods described here may use one or more devices or elements described in U.S. patent application Ser. No. 13/298,169, filed on Nov. 16, 2011 and titled "DEVICES AND METHODS FOR FORMING A FISTULA," now issued as U.S. Pat. No. 9,017,323, one or more devices or elements described in U.S. patent application Ser. No. 14/214,503, filed on Mar. 14, 2014 and titled "FISTULA FORMULATION DEVICES AND METHODS THEREFOR," one or more devices or elements described in U.S. Provisional Application Ser. No. 62/279,603, filed on Jan. 15, 2016 and titled "DEVICES AND METHODS FOR FORMING A FISTULA," and/or one or more devices or elements described in U.S. patent application Ser. No. 14/657,997, filed Mar. 13, 2015 and titled "FISTULA FORMATION DEVICES AND METHODS THEREFOR," each of which is hereby incorporated by reference in its entirety.

In some variations, a catheter may comprise one or more magnetic alignment components. In the variation of system (200) shown in FIG. 2, each of first (202) and second (203) catheters may comprise a plurality of magnetic alignment elements (212). These magnetic alignment elements (212) may be configured to bias the axial positioning of the first (202) and second (203) catheters such that the opening (205) of the first catheter (202) axially aligns with the recess (210) of the second catheter (203). The magnetic alignment elements (212) may also be configured to bias the rotational positioning of the first (202) and second (203) catheters such that the opening (205) of the first catheter (202) faces toward the recess (210) of the second catheter (203). Accordingly, the magnetic alignment elements (212) may be used to help position the first (202) and second (203) catheters within respective blood vessels such that the electrode (206) may be extended from opening (205) toward recess (210) of the second catheter (203) during fistula formation.

Other examples of magnet arrangements for use with the catheters described here may be found in in U.S. patent application Ser. No. 13/298,169, which was previously incorporated by reference in its entirety. Other examples of magnet arrangements for use with the catheters described here may be found in U.S. patent application Ser. No. 14/214,503 and U.S. patent application Ser. No. 14/657,997, both of which were previously incorporated by reference in their entirety. These magnetic alignment components may be attracted to one or more additional elements (e.g., one or more portions of a second catheter, one or more magnets or other components placed externally from the body) to help position or align the catheter within a vessel. For example, one or more magnetic alignment elements of a first catheter may interact with one or more magnetic alignment elements of a second catheter to attract the first and second catheters toward each other, and/or to bias the first and second catheters toward a specific rotational and/or axial alignment.

In some variations, one or more portions of the catheter may comprise a marker made, for example, from an echogenic or radiographic material. In one variation of system (200) shown above in FIG. 2, each of the first (202) and second (203) catheters may comprise one or more markers (214). These markers (214) may be visualized during advancement and/or position of the first (202) and second (203) catheters to confirm that the catheters are properly positioned within the blood vessels. A marker may be attached to the catheter by any suitable method, for example, by mechanical attachment (e.g., embedded in a portion of the catheter, circumferential circumscription, or the like), adhesive bonding, welding, soldering, combinations thereof or the like. Markers may be located anywhere relative to the catheter (e.g., one or more surfaces of the catheter, inside of the catheter).

II. Methods

Generally described here are methods for treating hypertension by reducing blood pressure by formation of one or more fistulas. The methods described here may include selecting a patient who may benefit from a lower blood pressure level. The methods described here may be particularly useful for patients suffering from higher levels of hypertension who may see a greater treatment effect, as well as for patients for which other hypertension treatments have been insufficient. In some variations, a desired reduction in blood pressure may be achieved by selection of a fistula location (i.e., blood vessels in which a fistula is to be located), as well as fistula characteristics such as size and number of fistulas. In some cases, formation of one or more fistulas may reduce blood pressure by a desired amount without further modification. In other cases, blood flow may be titrated after fistula formation to reduce blood pressure by a desired amount, as described in more detail herein.

A fistula may be formed between two blood vessels using one or more of the catheters described above to reduce blood pressure. The fistula and corresponding blood pressure reduction may be customized for a particular patient. For example, blood pressure reduction based on fistula formation may be customized based on a treatment goal, anatomical location, vessel compliance, and/or the size, shape, number, and/or arrangement of the fistula(s). The methods described may provide an alternative and/or additional treatment option for hypertension patients.

It should be appreciated that the methods described here may be used to form a fistula between an artery and vein that may not require a stent or other connecting structure to maintain patency of the fistula. As such, the formed fistula may be circumferentially or otherwise unrestrained by a stent, such that the fistula may conform its natural size and/or shape to the area of the arterial inflow. In other words, the pressure within the blood vessels may cause the size and/or shape of the unrestrained fistula to change after the fistula is formed. In some variations, this natural adjustment of size and/or shape of a fistula may be desirable as it increases fistula patency and longevity. However, it should be appreciated that in other variations, this natural adjustment of an unstented fistula may desirably be limited, such as through the techniques discussed in more detail herein. Additionally, an unstented fistula may result in a lowered risk of complications compared to a stented fistula. A stented fistula may cause more pronounced hemodynamic effects and augmented shear stress within the treated blood vessels, while in contrast, an unstented fistula may result in lower shear stress within the treated blood vessels, which may reduce the risk of stenosis and other adverse effects.

Patient Selection

Generally, a patient may be selected for treatment on the basis of a diagnosis of hypertension. For example, a patient having a systolic blood pressure of more than about 150 mmHg may be selected for the methods of treatment described herein. In other variations, a patient having a systolic blood pressure of more than about 160 mmHg may be selected. In yet other variations, a patient having a systolic blood pressure of more than about 170 mmHg may be selected. As another example, a patient having hypertension resistant to other treatments may be selected. In some variations, for instance, a patient with blood pressure of more than about 150 mmHg despite the use of a diuretic and at least two other blood pressure medications may be selected. In some variations, a patient with blood pressure controlled by blood pressure medications (e.g., four or more medications) may be selected for treatment.

In some variations, patient selection may be based on one or more demographic characteristics such as systolic blood pressure, diastolic blood pressure, and/or body mass index (BMI). In some circumstances, patients suffering from hypertension may also concurrently suffer from other conditions such as diabetes, coronary artery disease, and the like. In some variations, the methods may comprise selecting a patient having hypertension and one or more conditions including diabetes, pre-dialysis, hyperlipidemia, renal transplant, smoker (current or previous), and prior formation of an arteriovenous fistula. The methods need not be limited with respect to patient age or body mass index. However, in some variations, the methods may be performed on a patient that is under about 80 years old. In other variations, the patient may have a BMI of less than about 35.

Target Blood Pressure/Desired Reduction

The methods of treatment described herein may comprise determining a target blood pressure. For instance, in some variations, the target blood pressure is a systolic blood pressure at or below about 160 mmHg, and a diastolic blood pressure at or below about 100 mmHg. In some variations, the target blood pressure is a systolic blood pressure at or below about 150 mmHg, and a diastolic blood pressure at or below about 110 mmHg. In some variations, the target blood pressure is a systolic blood pressure at or below about 140 mmHg, and a diastolic blood pressure at or below about 90 mmHg. In some variations, the target blood pressure is a systolic blood pressure at or below about 120 mmHg, and a diastolic blood pressure at or below about 80 mmHg.

The target blood pressure may be used to determine a desired overall blood pressure reduction—that is, the difference between a patient's baseline blood pressure and the target blood pressure. The target blood pressure and treatment plan may be used to determine a desired blood pressure reduction due to fistula formation. In some variations, fistula formation may be used alone for reducing blood pressure (i.e., may be the only hypertension treatment), and thus, the desired blood pressure reduction due to fistula formation may be equal to the desired overall blood pressure reduction. In other variations, fistula formation may be used in combination with one or more hypertension treatments (e.g., drug, diet, behavior). For instance, hypertensive patients may take one or more medications in addition to having one or more fistulas formed. In these cases, fistula formation may account for a portion of the overall desired blood pressure reduction.

Patients suffering from a higher degree of hypertension may benefit from a larger drop in blood pressure. For example, a patient having a baseline systolic blood pressure of 195 mmHg may have a target systolic blood pressure of 155 mmHg. The desired overall blood pressure reduction is thus 40 mmHg. In this example, fistula size, number, and location are selected to provide the entire desired 40 mmHg reduction in blood pressure such that the desired overall blood pressure reduction is entirely due to fistula formation.

In another example, a patient having a baseline systolic blood pressure of 180 mmHg may have a target systolic blood pressure of 150 mmHg for a desired overall blood pressure reduction of 30 mmHg. The treatment plan may be designed to provide 20 mmHg of blood pressure reduction through fistula formation and 10 mmHg of blood pressure reduction through medication. In this case, fistula formation accounts for two-thirds of the overall desired blood pressure reduction.

In some variations, a fistula may be configured to reduce blood pressure by about at least 5% from a baseline blood pressure. In some variations, a fistula may be configured to reduce blood pressure by about at least 10% from a baseline blood pressure. In some variations, a fistula may be configured to reduce blood pressure by about at least 15% from a baseline blood pressure. In some variations, a fistula may be configured to reduce blood pressure by about at least 20% from a baseline blood pressure. In some variations, a fistula may be configured to reduce blood pressure by about at least 25% from a baseline blood pressure. In some variations, a fistula may be configured to reduce blood pressure by about at least 30% from a baseline blood pressure.

In some variations, the methods of treatment described here may cause a decrease in baseline blood pressure immediately after fistula formation and may be measured by a catheter after fistula formation. In some variations, the full reduction in blood pressure may be achieved after fistula maturation, e.g., after about 30 days from formation. The reduction in blood pressure due to fistula formation may be a sustained effect. That is, the reduction in blood pressure may persist for months or years after fistula formation. Fistula maturation may depend on vessel composition, flow rate and fistula size.

In some variations, the methods of treatment described here may cause a decrease in blood pressure through a series of procedures over time. For example, a first fistula may be formed in a first procedure to provide a first reduction in blood pressure. After a predetermined period of time, additional procedures may be performed to modify the vessels and/or create additional fistulas to reach a desired overall blood pressure reduction.

Fistula Location

In some variations of the methods described herein, the location at which one or more fistulas are formed may be determined based on the blood pressure reduction desired to be achieved by fistula formation. That is, the methods of treating hypertension described herein may comprise selecting blood vessels for fistula formation based on a desired amount of blood pressure reduction. Certain blood vessels within the cardiovascular system may be more effective in reducing blood pressure. The location of fistula formation may be selected based on one or more factors. For instance, the characteristics of the blood vessels including their size, length, composition, and/or their interaction with other vessels within the vascular system may affect a change in blood pressure effected by fistula formation.

In some instances, appropriate selection of vessels for fistula formation may be important to achieve the desired blood pressure reduction without undesirable complications. In some of the methods described herein, vessels for fistula formation may be selected at least in part based on the length and diameter of the vessels. The selection of small diameter blood vessels (e.g., less than 0.5 mm in diameter) for fistula formation may provide high fluidic resistance proximal to the fistula that may restrict the development of high fistula blood flow, such that an observable reduction in blood pressure may be unlikely. Furthermore, fistula closure via thrombosis is more likely with small diameter blood vessels. Conversely, selection of large blood vessels (e.g., greater than 2 mm in diameter) for fistula formation may provide a fistula resistance that dominates a blood flow rate. This may be undesirable where fistula flow is highly dependent on fistula resistance, as opposed to other resistances in the fluid network. For example, enlargement of the fistula by maturation or dilation may reduce fistula resistance unpredictably and result in undesirably high flow rates through the fistula. Excessive flow through the fistula may lead to high output cardiac failure (HOCF), hypotension, venous stenosis via turbulent shear along the vessel walls, and steal syndrome that prevents adequate perfusion to distal extremities.

Thus, blood vessels for fistula formulation may be selected based on vessel diameter and/or length. For instance, in some variations, the methods described herein may comprise forming a fistula between vessels having diameters of approximately 1 mm or greater. More specifically, the method may comprise forming a fistula between vessels having diameters of approximately 2 mm to 3 mm.

In some variations, the blood vessels selected for fistula formation may be based on the structural composition of blood vessels. Generally, large vessels in close proximity to the heart have a high degree of compliance that allows them to expand radially and axially for volumetrically storing the pulsatile output of the heart and maintaining arterial pressure during diastole. These vessels contain a high elastin/collagen ratio and are collectively described as elastic arteries. Towards the periphery of the vascular system, there is a gradual transition in the arteries to those with walls composed of a significantly higher percentage of smooth muscle cells controlled by the sympathetic nervous system for constricting and expanding the arterial lumen diameter to control blood flow to the periphery. These vessels are collectively described as muscular arteries. The enlargement and/or dilation of a fistula may be different between a muscular artery and an elastic artery and may be controlled by modifying the vessel such as through heat shrinking, described in further detail herein. As described in more detail herein, fistula size may affect the amount of blood pressure reduction caused by the fistula.

In some variations, the blood vessels selected for fistula formation may be based on their location within the vasculature, that is, the anatomical location of the fistula within an artery-vein network. In some variations of the methods described herein, blood vessels for fistula formation may be selected based on a model of the vascular network. An expected reduction in blood pressure due to fistula formation may be determined from the model for a fistula having the characteristics as described herein between two vessels and its location within those vessels. For instance, blood flow rate through a fistula may depend on the fistula's own resistance, arterial vessel resistance, and venous vessel resistance. Fistula resistance may be based on fistula characteristics described herein, arterial vessel resistance may be based on arterial vessel resistances proximal the fistula, and venous vessel resistance may be based on venous vessel resistances proximal the fistula. Determination of flow rate through the network allows a corresponding blood pressure to be determined.

Figure 4A:
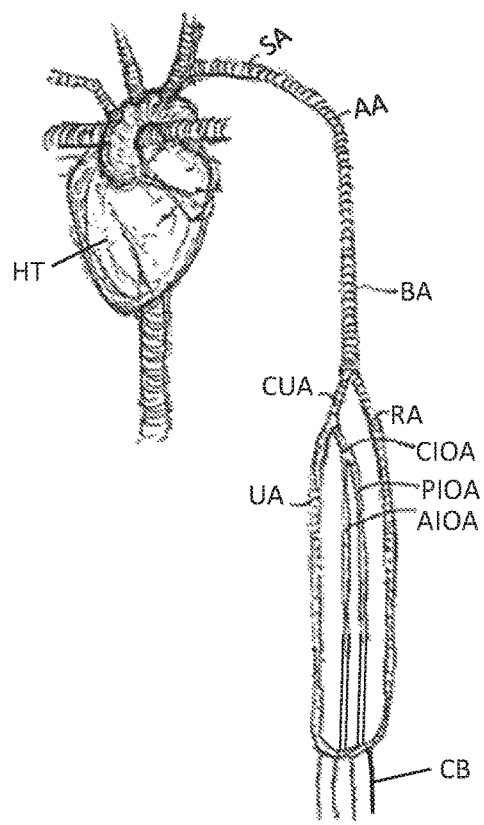

As an example, FIG. 4A illustrates an illustrative arterial network of the arm. The subclavian artery (SA) is connected to the heart (HT) and provides blood flow through the axillary artery (AA) and subsequently through the brachial artery (BA). The brachial artery (BA) branches into the common ulnar artery (CUA) and radial artery (RA). The common ulnar artery (CUA) then branches into the ulnar artery (UA) and the common interosseous artery (CIOA). The common interosseous artery (CIOA) thereafter branches into the posterior interosseous artery (PIOA) and the anterior interosseous artery (AIOA). The capillary bed (CB) receives blood flow from each of the ulnar artery (UA), the anterior interosseous artery (AIOA), the posterior interosseous artery (PIOA), and the radial artery (RA).

Figure 4B:
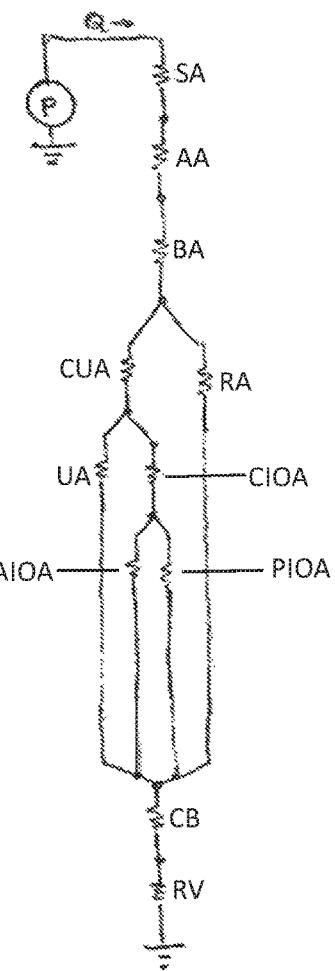

The arterial network in FIG. 4A may be represented as a lumped parameter model in FIG. 4B that is analogous to an electrical circuit. As shown there, the blood vessels are represented by resistances, the heart is represented by a pump (P) corresponding to a voltage source, and blood flow (Q) corresponds to current. FIG. 4B illustrates blood flow (Q) through a series connection of the subclavian artery (SA), the axillary artery (AA), and the brachial artery (BA). The brachial artery (BA) branches into the common ulnar artery (CUA) and the radial artery (RA). The common ulnar artery (CUA) branches into the ulnar artery (UA) and the common interosseous artery (CIOA), which further branches into the anterior interosseous artery (AIOA) and the posterior interosseous artery (PIOA). The capillary bed (CB) receives blood flow from each of the ulnar artery (UA), the anterior interosseous artery (AIOA), the posterior interosseous artery (PIOA), and the radial artery (RA). The capillary bed (CB) connects in series to the radial vein (RV). From this model, arterial vessel resistances may be determined for a potential fistula location in the arterial network. In particular, vessel resistance may be determined for an arterial vessel and for a fistula location along the length of the selected arterial vessel. A model of the arteriovenous fistula network is discussed further below with respect to FIG. 4E.

FIG. 4C illustrates a radial artery-vein network and FIG. 4D illustrates a corresponding lumped parameter model. In FIG. 4C, a basilic vein (BASV) joins a cephalic vein (CV) at perforating veins (PV). A first and second brachial vein (BV) connects to respective first and second radial veins (RV1, RV2). The radial artery (RA) is located adjacent to the radial veins (RV1, RV2). In FIG. 4D, the basilic vein (BASV) and cephalic vein (CV) join at the perforating vein (P). A first brachial vein (BV1) and second brachial vein (BV2) also connect to the perforating vein (P) and receive venous blood flow from radial vein (RV). FIG. 4D thus illustrates four pathways for venous blood flow from the radial vein (RV) to the central nervous system.

Although not shown in FIG. 4D, a fistula formed in the radial vein (RV) connected to a parallel network of return vessels allows the arterial flow from the radial artery (RA) to be diffused amongst multiple veins (BV1, BV2, BaV, CV) so as to effectively reduce the wall shear stress in each vessel. Lowering wall shear stress in turn reduces the likelihood of venous stenosis. Diffusion of arterial inflow may thus reduce the need to occlude or coil embolize the artery and/or vein proximal to the fistula that would reduce the blood flow rate through the venous network. From this model, venous resistance may be determined for a potential fistula location in the venous network. In particular, vessel resistance may be determined for a venous vessel and for a fistula location along the length of the selected venous vessel. The lumped parameter models shown in FIGS. 4B and 4D are combined below in FIG. 4E, and include an illustrative fistula that allow modeling of fluid flow through the fistula and entire network.

Figure 4E:
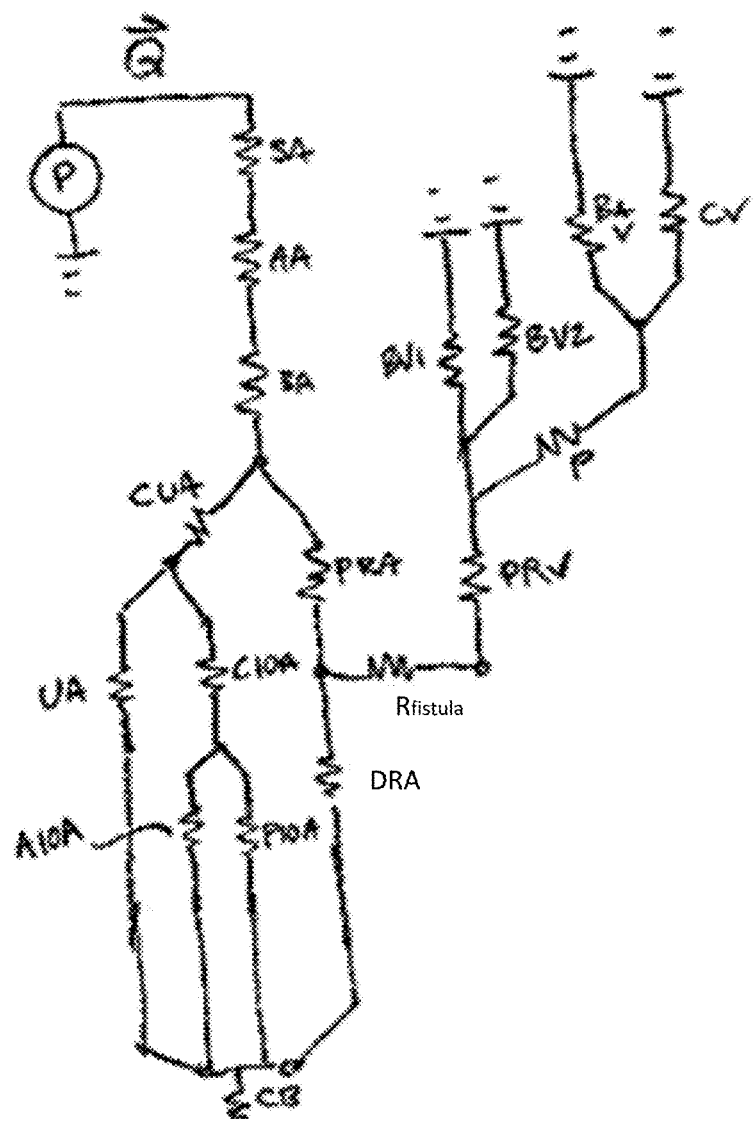

FIG. 4E is a lumped parameter model for a fistula formed in a radial artery-radial vein location that allows an expected reduction in blood pressure to be determined. Fluid resistance and blood flow may vary based on the selected fistula location. In a lumped parameter model, a fistula may be conceptualized as forming a resistance shunt between the high-pressure arterial and low-pressure venous cardiovascular network that may generate large flow rates through the fistula. Given that the heart is a positive displacement pump, creation of a parallel low resistance pathway to the capacitive venous reservoir may decrease arterial pressure. The fistulas formed as described here offer a low resistance pathway for blood to preferentially flow. A fistula is modeled as having a resistance $R_{fistula}$ between a radial artery (RA) and a radial vein (RV). The fistula divides the artery into a proximal radial artery (PRA) and a distal radial artery (DRA). Similarly, the fistula connects to a proximal radial vein (PRV). The fistula may be formed having a resistance $R_{fistula}$ generating a corresponding change in blood flow that reduces pressure in the fistula network and provides a corresponding drop in blood pressure.

In some variations, the location of the fistula may be selected such that the resistances of the proximal radial artery (PRA) and proximal radial vein (PRV) are such that they limit the sensitivity of $R_{fistula}$ on the fistula network. In other words, the location of the fistula may be selected such that $R_{fistula}$ provides a predetermined portion of the total resistance of the fistula network. In some cases, a change in $R_{fistula}$ due to maturation of the fistula may have a reduced effect on blood flow (Q). As discussed above, a desired amount of change in blood pressure may be based on the location of the fistula within a network of blood vessels. In one variation, the resistance of the proximal vessels in a fistula network may dominate over a fistula resistance. For instance, a proximal blood vessel network resistance may substantially determine blood flow rate when a fistula is formed of such a large size that the fistula resistance is negligible.

In other variations, to limit the sensitivity of the fistula network fluid resistance to changes in fistula resistance ($R_{fistula}$), the resistance provided by the proximal blood vessels in a fistula network comprise about at least half of the total fistula network resistance. In this case, the resistance of the network would remain bound by the vessel resistances, even if the fistula were enlarged such that $R_{fistula}$ was reduced to a negligible value.

In some variations, a mapping of a patient artery-vein network may be performed to generate a patient's lumped parameter model of a fistula network. The artery-vein mapping may be performed by ultrasound, CT fluoroscopy, or the like. The mapped network may then be used to determine the location of the one or more fistulas.

Fistula location and characteristics may thus be selected based on the considerations described herein. The model is not particularly limited by the number of fistulas formed. In some variations, a fistula may be formed at a site in the proximal ulnar artery. As used herein, the term "proximal ulnar artery" means the ulnar artery between the brachial artery and branch of the interosseous artery. In some variations, a fistula may be formed between an ulnar artery and a deep ulnar vein. In these variations, it may be desirable to form a fistula at a location within about 6 cm from the branch between the brachial artery and the ulnar artery. In some of these variations, the fistula may be formed at a location less than about 4 cm from the branch between the brachial artery and the ulnar artery.

In some variations, fistulas may be formed using one or more deep veins, such as the deep ulnar vein. Due to their deep anatomic location, the deep ulnar veins are difficult to access surgically, and thus are not traditionally desirable target sites for surgical fistula-forming techniques. The deep anatomic location of the deep ulnar veins, however, means that these veins are usually undamaged (e.g., by needle sticks or other trauma), which may increase fistula longevity. A fistula located in the deep system may also reduce the risk of extravasation. In some instances, each of the deep ulnar veins may be utilized to form different fistulas as both of the deep ulnar veins feed into the cephalic and basilic venous systems. However, it should be appreciated that the blood vessels in which the fistula is to be formed are not limited to the ulnar artery and veins. In some variations, the methods described herein comprises forming one or more fistulas between a radial artery and a radial vein to treat hypertension. In other variations, the method comprises forming one or more fistulas between any suitable artery and any suitable deep vein. For example, based on a desired reduction in blood pressure, one or more fistulas may be formed between the distal radial artery and the radial vein; the distal ulnar artery and the ulnar vein; the proximal radial artery and the radial vein; the proximal ulnar artery and the ulnar vein; the common ulnar artery and the common ulnar vein; the distal radial artery and the cephalic vein; the brachial artery and the brachial vein; the tibial artery and the tibial vein; the femoral artery and the femoral vein; the iliac artery and the iliac vein; the pulmonary artery and the pulmonary vein; the interosseous artery and the interosseous vein; and/or the brachial artery and the basilic vein. Formation of one or more fistulas between the brachial artery and brachial vein, for example, may provide a higher flow rate due to the vessels' large diameters, and thus may have lower resistance. Formation of one more fistulas between the brachial artery and brachial vein may thus result in a greater drop in blood pressure as compared to between vessels of smaller diameters.

Fistula Characteristics

In some variations, the methods described herein may comprise forming one or more fistulas having one or more characteristics selected based on a desired amount of blood pressure reduction. For example, the fistula size (e.g., length, width), number of fistulas, spacing between fistulas, and/or overall arrangement or pattern of the fistulas may be selected in a manner to cause a desired increase in arterial inflow, and in turn, a desired reduction in blood pressure. That is, a change in blood pressure may be achieved by changing systemic vascular resistance through selection of fistula characteristic(s).

In some variations, the fistulas formed during the methods described herein may have sizes (i.e., cross-sectional area) selected based on a desired blood pressure reduction. For example, increasing the size of a fistula generally increases a fistula flow rate and decreases fistula flow resistance, which may in some instances result in a greater drop in blood pressure. However, in some variations the magnitude of such an effect may be influenced by the size of the vessels between which the fistula is formed. In some cases, for example, the fluid flow rate through a fistula may be limited by the size of the vessels rather than by the size of the fistula. This may be the case in variations in which a fistula having a relatively large fistula aperture is formed in small diameter vessels. For example, fluid flow rate through a fistula may be limited by the vessels when the vessel diameters are about 2 mm and the fistula has a diameter of 5-8 mm. It should be appreciated that in some variations, the size of a fistula may change after it is initially formed, as described in more detail herein.

In some variations, the fistulas formed by the methods described herein may have sizes (i.e., cross-sectional area) selected based on a desired blood pressure reduction for a given hypertensive patient at a predetermined fistula location (e.g., ulnar artery-ulnar vein). In some variations, a computational model using a distributed lumped parameter method may be used to determine a desired fistula size based on a hypertensive patient's baseline blood pressure and a desired blood pressure reduction. FIGS. 9-12 illustrate such a model for an ulnar artery-ulnar vein fistula with simulated patients.

Figure 9:
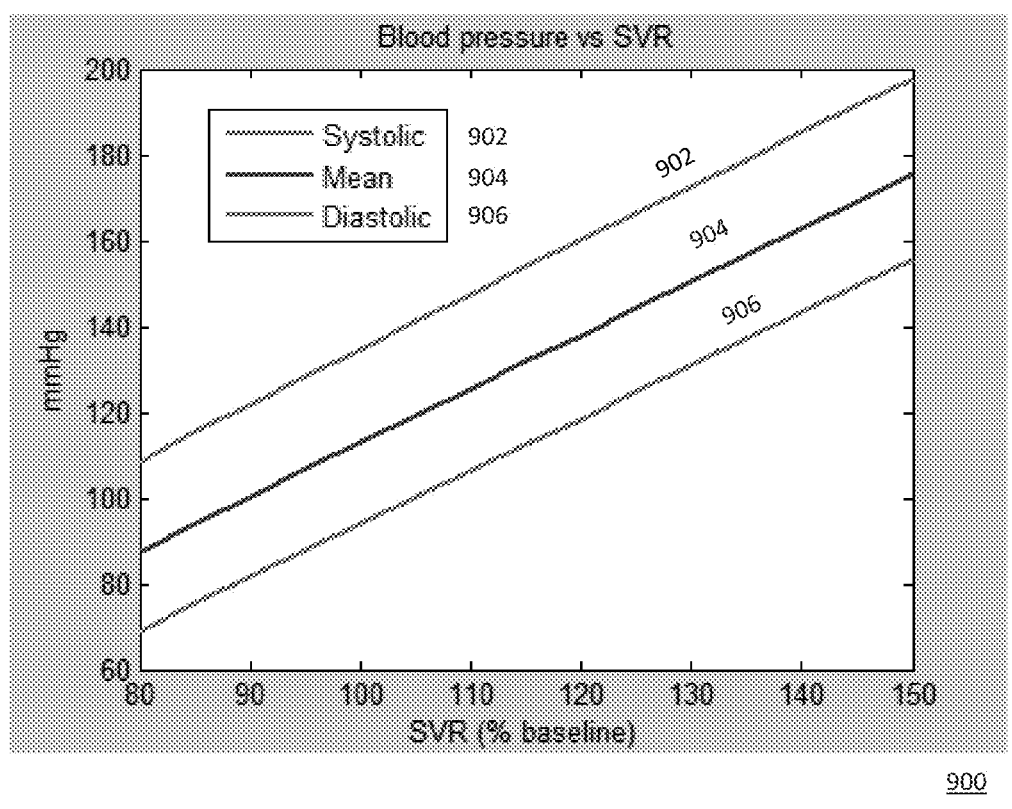
FIG. 9 is an illustrative graph of blood pressure as a function of systemic vascular resistance.

FIG. 9 shows a baseline hemodynamics model simulating systolic blood pressure (902), mean blood pressure (904), and diastolic blood pressure (906) as a function of SVR without a fistula. Patients were simulated as having a range of SVR, BV, and LVE. Table 1 below lists a set of patients (1-8) having varying values of systemic vascular resistance (SVR), blood volume adjustment (BV), and LV elastance (LVE):

TABLE 1

|        | 1    | 2    | 3    | 4    | 5    | 6    | 7    | 8    |
|--------|------|------|------|------|------|------|------|------|
| SVR    | 80%  | 90%  | 100% | 110% | 120% | 130% | 140% | 150% |
| BV(ml) | −200 | −100 | 0    | 100  | 200  | 300  | 400  | 500  |
| LVE    | 90%  | 95%  | 100% | 105% | 110% | 115% | 120% | 125% |

When the model is used to simulate a system without a fistula, the cardiac output may be nearly constant and have a range of about 5.00 L/min to about 5.15 L/min, while the systolic blood pressure may vary from approximately 110 mmHg to 200 mmHg.

Figure 10:
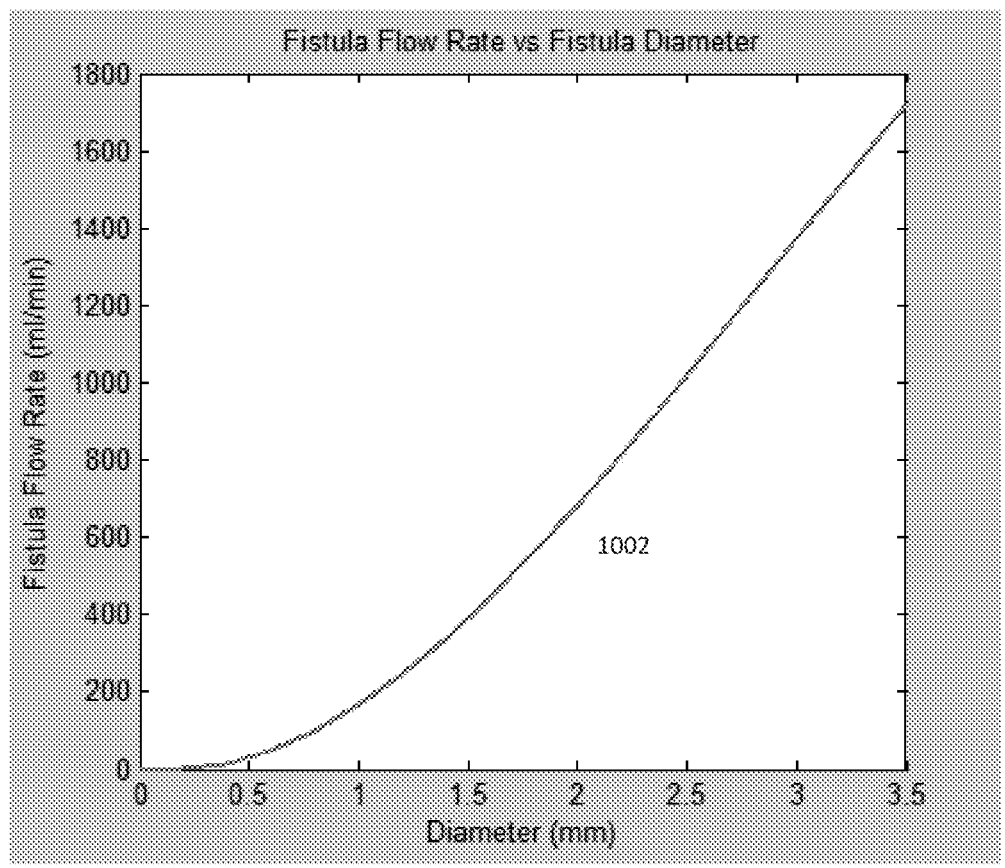
FIG. 10 is an illustrative graph of fistula flow rate as a function of fistula diameter.

FIG. 10 is an illustrative graph (1000) of fistula flow rate as a function of fistula size. For simulated patient 3 of Table 1 having values of 100% baseline SVR, 0 BV, and 100% baseline LVE, for example, FIG. 10 shows fistula flow rate for fistula diameters varying from 0 mm to 3.5 mm. A larger fistula generally provides a larger flow rate as represented in FIG. 10 by the non-linear curve (1002). For the sake of clarity, flow rate as a function of fistula size is provided in FIG. 10 only for simulated patient 3. Similar graphs may be formed for simulated patients 1-2, 4-8 as well as simulated patients having characteristics other than those shown in Table 1.

Figure 11A:
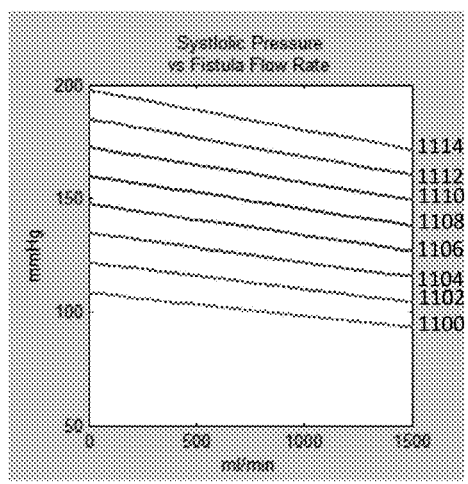
FIGS. 11A-11F depict illustrative graphs of arterial blood pressure as a function of fistula flow rate.
Figure 11B:
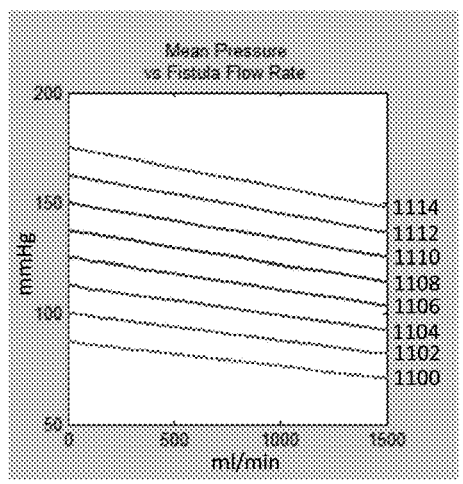
Figure 11C:
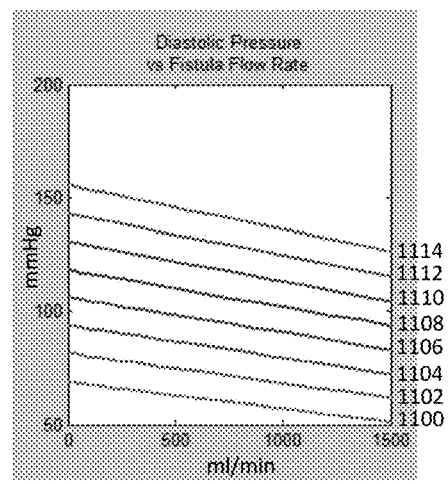
Figure 11D:
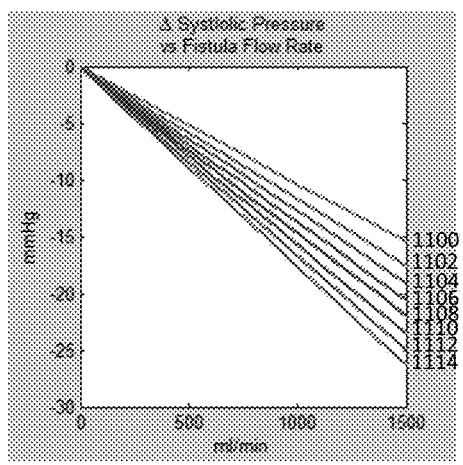
Figure 11E:
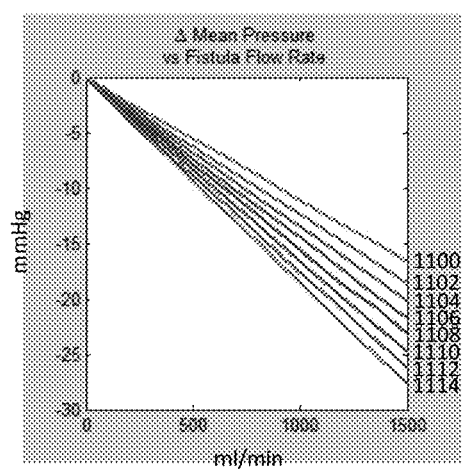
Figure 11F:
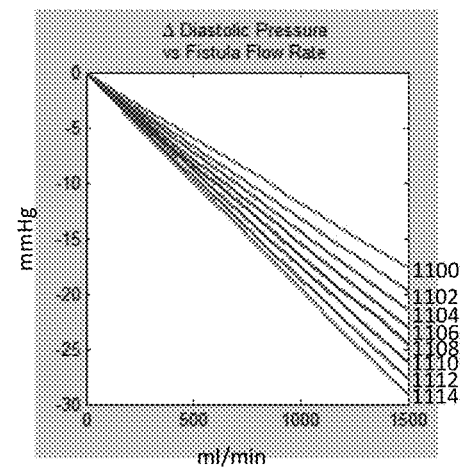

FIGS. 11A-11F depict six illustrative graphs of arterial blood pressure as a function of fistula flow rate for systolic pressure (FIG. 11A), mean pressure (FIG. 11B), and diastolic pressure (FIG. 11C), a change in systolic pressure (FIG. 11D), a change in mean pressure (FIG. 11E), and a change in diastolic pressure (FIG. 11F) for each of the simulated patients (1-8) listed in Table 1. Each simulated patient (1, 2, 3, . . . 8) listed in Table 1 is represented by a corresponding curve (1100, 1102, 1104, . . . 1114). FIGS. 11D-11F illustrate an amount of arterial blood pressure reduction that may be obtained as a function of fistula flow rate. Generally, a higher baseline blood pressure results in a greater reduction in blood pressure. Thus, fistula characteristics such as size may be determined based on a desired amount of blood pressure reduction for patients having hypertension.

Figure 12A:
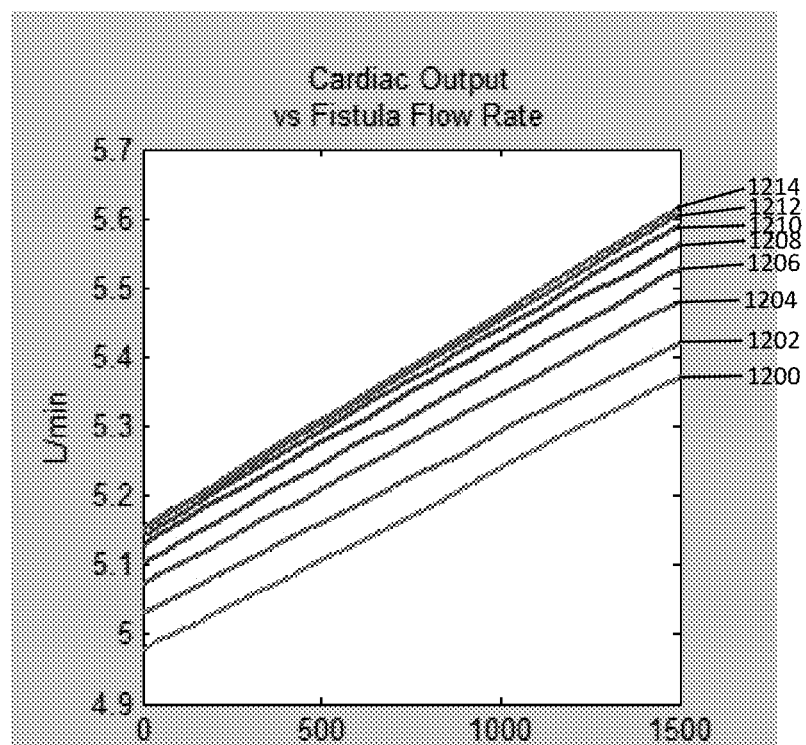
FIGS. 12A-12B depicts illustrative graphs of cardiac output as a function of fistula flow rate.
Figure 12B:
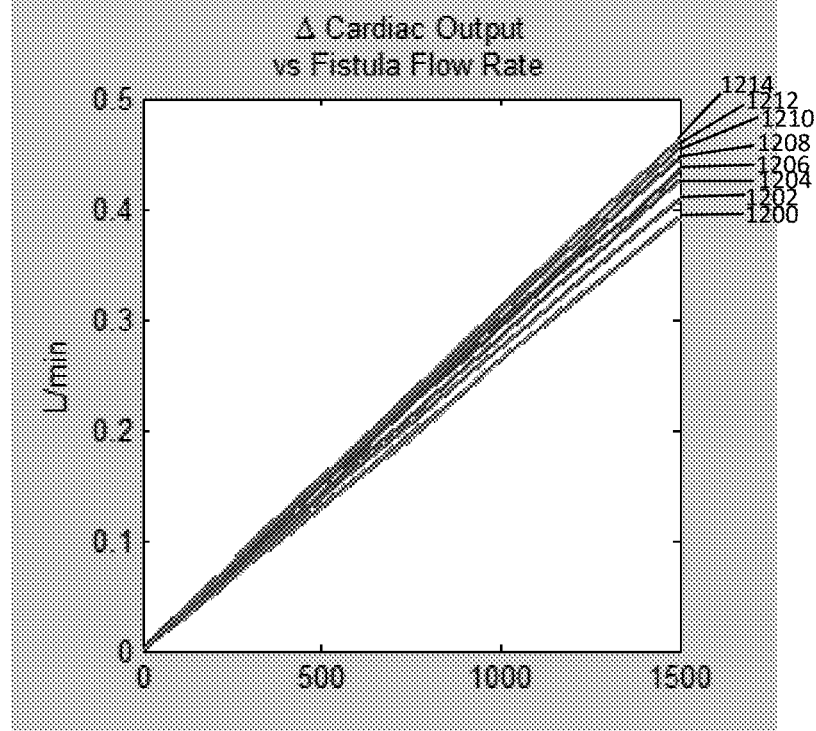

FIGS. 12A-12B depict cardiac output (FIG. 12A) and a change in cardiac output (FIG. 12B) as a function of fistula flow rate for each of the simulated patients (1-8) listed in Table 1. Cardiac output (CO) describes the volume of blood being pumped by the heart per unit time. Each simulated patient (1, 2, 3, . . . 8) is represented by a corresponding curve (1200, 1202, 1204, . . . 1214). In particular, the model shows that the baseline cardiac output before fistula formation may increase by about 30% of the fistula flow rate after fistula formation. FIG. 12B shows patients having higher degrees of baseline hypertension, such as patient 8 corresponding to curve (1214), may have a greater change in cardiac output after fistula formation, especially at higher flow rates.

In some variations, methods of treating hypertension may comprise forming a plurality of fistulas. In these cases, the number and relative location of the plurality of fistulas may be selected based on the desired blood pressure reduction. In some variations, each fistula in a plurality of fistulas may be formed between different vessels. In other variations, each fistula in a plurality of fistulas may be formed between the same vessels. For example, a plurality of fistulas may be formed between an artery and a vein, such that increased arterial inflow may be divided among the fistulas. In yet other variations, a plurality of fistulas may be formed both between the same vessels and between different vessels. In variations in which a plurality of fistulas are formed, the fistulas may have the same or different shapes, sizes, spacing, and arrangement.

Figure 5A:
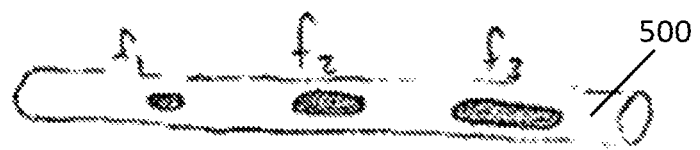
FIGS. 5A-5C depict illustrative variations of fistulas formed in a vessel and a corresponding lumped parameter model.
Figure 5B:
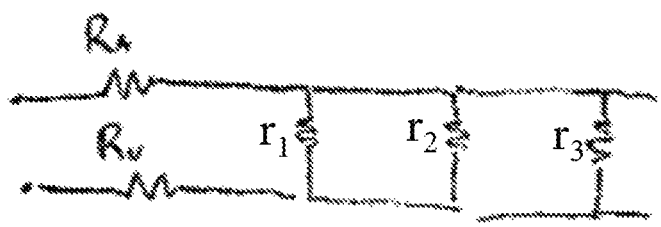
Figure 5C:
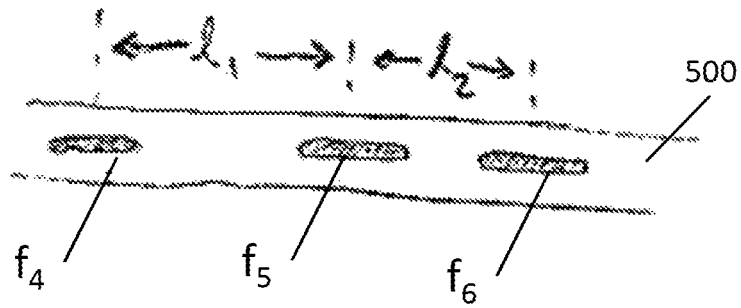

In some variations, as shown in FIG. 5A, a plurality of fistulas may be located consecutively or sequentially so as to be located axially along the blood vessels (500) (e.g., arranged serially along the arm of the patient). FIG. 5A illustrates a plurality of fistulas (f1, f2, f3) formed as a series of fistulas located axially along the same vessels. (Only one vessel (500) is shown in FIGS. 5A and 5C for clarity.) When a plurality of fistulas are formed, the fistulas may have the same size, or they may have different sizes, as shown in FIG. 5A. Generally, an increase in the number of fistulas results in a greater reduction in blood pressure. In some instances, formation of a plurality of fistulas may offer benefits over formation of a single fistula. For example, the flow rate through each of the plurality of fistulas may have a reduced flow rate, which in turn may reduce shear stress and turbulence. This may have benefits such as a reduced the risk of stenosis. FIG. 5B illustrates a model of the fistula network of FIG. 5A. As shown there, the model includes arterial resistance (RA), venous resistance (RV), and parallel fistula resistances (r1, r2, r3). Accordingly, a desired fistula resistance may be achieved through the addition of parallel fistula resistances.

In some variations in which a plurality of fistulas are formed, the relative locations of the plurality of fistulas may be selected based on the desired blood pressure reduction.

FIG. 5C illustrates spacing between three fistulas ($f_4$, $f_5$, $f_6$), where fistulas $f_4$ and $f_5$ are separated by distance $l_1$, and fistulas $f_5$ and $f_6$ are separated by distance $l_2$. Generally, larger spacing between fistulas may increase resistance, and may thus result in a smaller reduction in blood pressure, while shorter spacing between fistulas may decrease resistance, and may thus result in a greater reduction in blood pressure.

In some variations, methods of treating hypertension may comprise forming any suitable number of fistulas between an ulnar artery and a deep ulnar vein or any suitable number of fistulas between a radial artery and a radial vein. For example, the method may comprise forming a first fistula, a second fistula, third fistula, or any suitable number of fistulas between an ulnar artery and a deep ulnar vein. As another example, the method may comprise forming a first fistula, a second fistula, a third fistula, or any suitable number of fistulas between a radial artery and a radial vein. In other variations, methods of treating hypertension may comprise forming a plurality of fistulas, where each fistula is formed between a different artery and respective vein. For example, the method may comprise forming a first fistula between an ulnar artery and a deep ulnar vein and forming a second fistula between a radial artery and a radial vein. The method may further comprise forming any suitable number of additional fistulas between the ulnar artery and the ulnar vein and/or forming any suitable number of additional fistulas between the radial artery and radial vein.

Furthermore, in some variations, the method may comprise forming multiple fistulas on the same side of a patient (e.g. same arm) and/or different sides of a patient (e.g., at least one fistula on a left arm and at least one fistula on a right arm). In some variations, the arrangement of multiple fistulas may divert flow from the artery into multiple deep veins, which may, in some instances, reduce overall shear stress within the veins as a result of the increased arterial flow.

The formation of a plurality of fistulas may additionally be desirable for other reasons. For example, formation of a plurality of fistulas may provide a backup in case one or more fistulas close. Additionally or alternatively, in some variations, formation of a plurality of fistulas may allow for easier tailoring of blood pressure reduction after initial formation of a fistula. For instance, one or more of the plurality of fistulas may be intentionally occluded to decrease fistula flow and increase fistula resistance as desired. Fistula occlusion may be performed in any suitable manner, such as but not limited to placement of a covered stent, or use of an embolization plug or coil that may fully or partially occlude a fistula. As another example, in some variations, one or more additional fistulas may be added after initial formation of one or a plurality of fistulas. In some variations, one or more additional fistulas may be occluded or formed during the same procedure as the initial fistula formation. For example, vascular resistance may be measured intra-operatively, and then based on the measurement, one or more fistulas may be formed or occluded. In other variations, one or more fistulas may be occluded or formed during a different, subsequent procedure. In these variations, the occlusion or formation of one or more fistulas may, for example, be based on blood pressure measurements performed after surgery, such as but not limited to after healing has taken place. For example, one or more fistulas may be occluded if an increase in blood pressure is desired (e.g., the initial blood pressure reduction was too large or became too large over time), or one or more additional fistulas may be formed if an additional reduction in blood pressure is desired (e.g., the initial blood pressure reduction was too small or became too small over time). Additionally or alternatively, the occlusion or formation of one or more fistulas may be based on determination of undesirably high flow rates through the one or more fistulas.

Catheter Advancement and Fistula Formation

Generally, methods of treating hypertension described here may comprise endovascularly advancing a distal portion of a first catheter into a first vein, endovascularly advancing a distal portion of a second catheter into an artery, and forming a fistula between the artery and the vein for reducing blood pressure. The catheters used in the methods described herein may be any of the catheters described herein or in U.S. patent application Ser. No. 13/298,169, U.S. patent application Ser. No. 14/214,503, U.S. Provisional Application Ser. No. 62/279,603, and/or U.S. patent application Ser. No. 14/657,997, each of which were previously incorporated by reference in their entirety. The first and second catheters may be advanced into any suitable pair of vessels, as described in more detail herein. For example, as mentioned above, in some variations of the method, a fistula may be formed between a proximal ulnar artery and a first deep ulnar vein, and thus the methods may comprise endovascularly advancing a distal portion of a first catheter into a first deep ulnar vein, endovascularly advancing a distal portion of a second catheter into a proximal ulnar artery, and forming a fistula between the proximal ulnar artery and the first deep ulnar vein. In other variations of the method, the fistula may be formed between a radial artery and a radial vein, and thus the methods may comprise endovascularly advancing a distal portion of a first catheter into a radial vein, endovascularly advancing a distal portion of a second catheter into a radial artery, and forming a fistula between the radial artery and the radial vein. Similarly, in other variations of the method, the fistula may be formed between any suitable artery and vein.

The first and second catheters may be aligned to position one or more fistula-forming elements (e.g., one or more electrodes, as described in more detail herein) relative to the desired fistula site. One or both of the first and second catheters may be advanced or retracted within their respective blood vessels to axially position the one or more fistula-forming elements relative to the fistula-formation site. One or both of the first and second catheters may be rotated to rotationally position the one or more fistula-forming elements relative to each other and to the fistula-formation site (e.g., to direct a fistula-forming element in the ulnar artery toward a deep ulnar vein, to direct a fistula-forming element in a deep ulnar vein toward the ulnar artery, to direct a fistula-forming element in the ulnar artery toward a fistula-forming element in a deep ulnar vein, etc.).

As described herein, the methods described here may utilize one or more catheters comprising one or more alignment elements, which may help to position catheters within the vasculature. For example, in some variations, a method may comprise using one or more alignment elements to help bring two or more catheters (and with them, associated blood vessels) in closer approximation. Additionally or alternatively, a method may comprise using one or more alignment elements to position one or more catheters in a specific rotational configuration relative to the blood vessels and/or the other catheter. Additionally or alternatively, a method may comprise using one or more alignment elements to position one or more catheters axially within a blood vessel or blood vessels. For example, one or more alignment elements may be configured to position a fistula-forming element of a catheter relative to the ulnar artery and a deep ulnar vein such that activation of the fistula-forming element directs fistula formation between the two vessels.

Figure 3A:
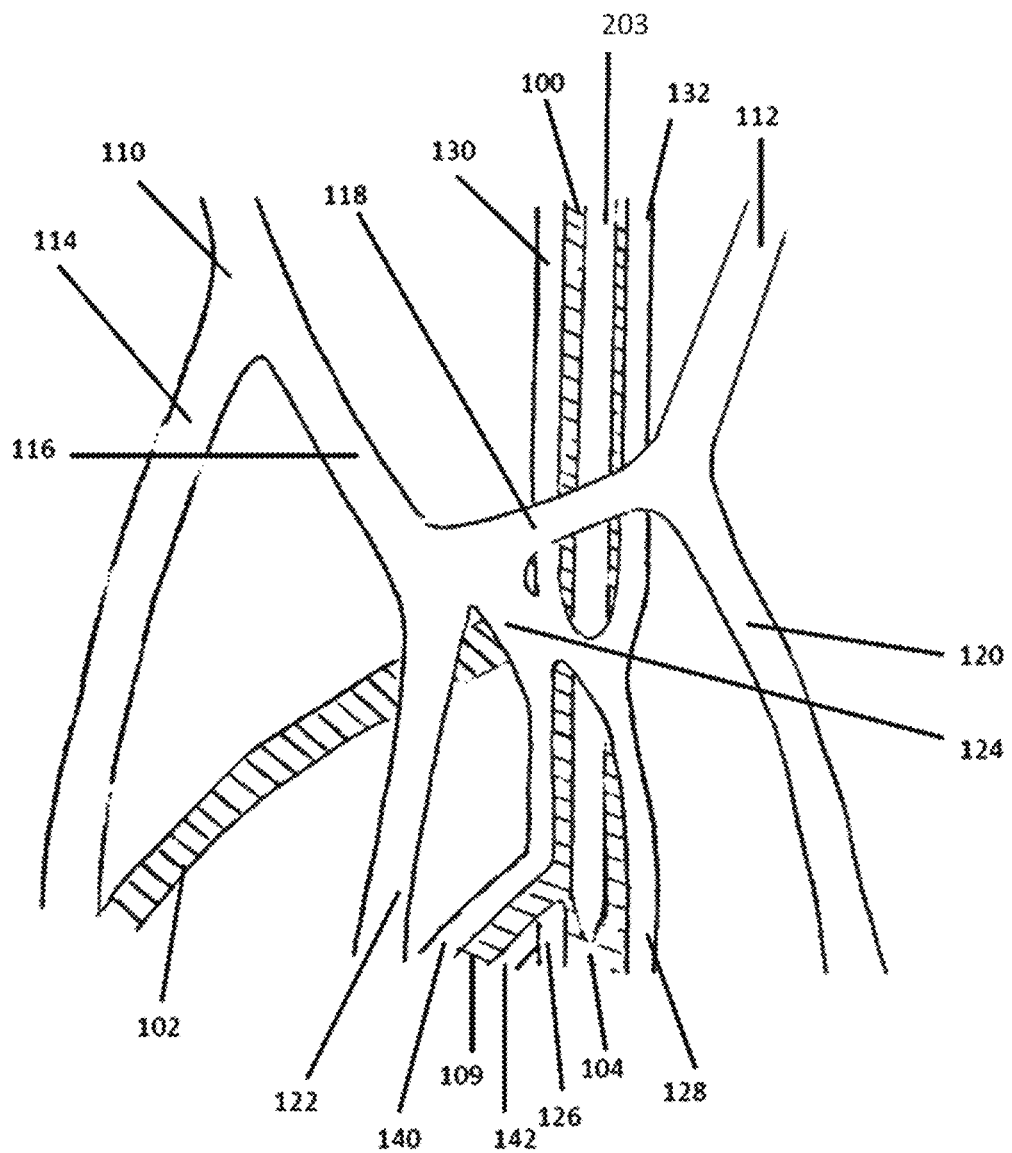
FIGS. 3A-3C depict an illustrative method as described here.
Figure 3B:
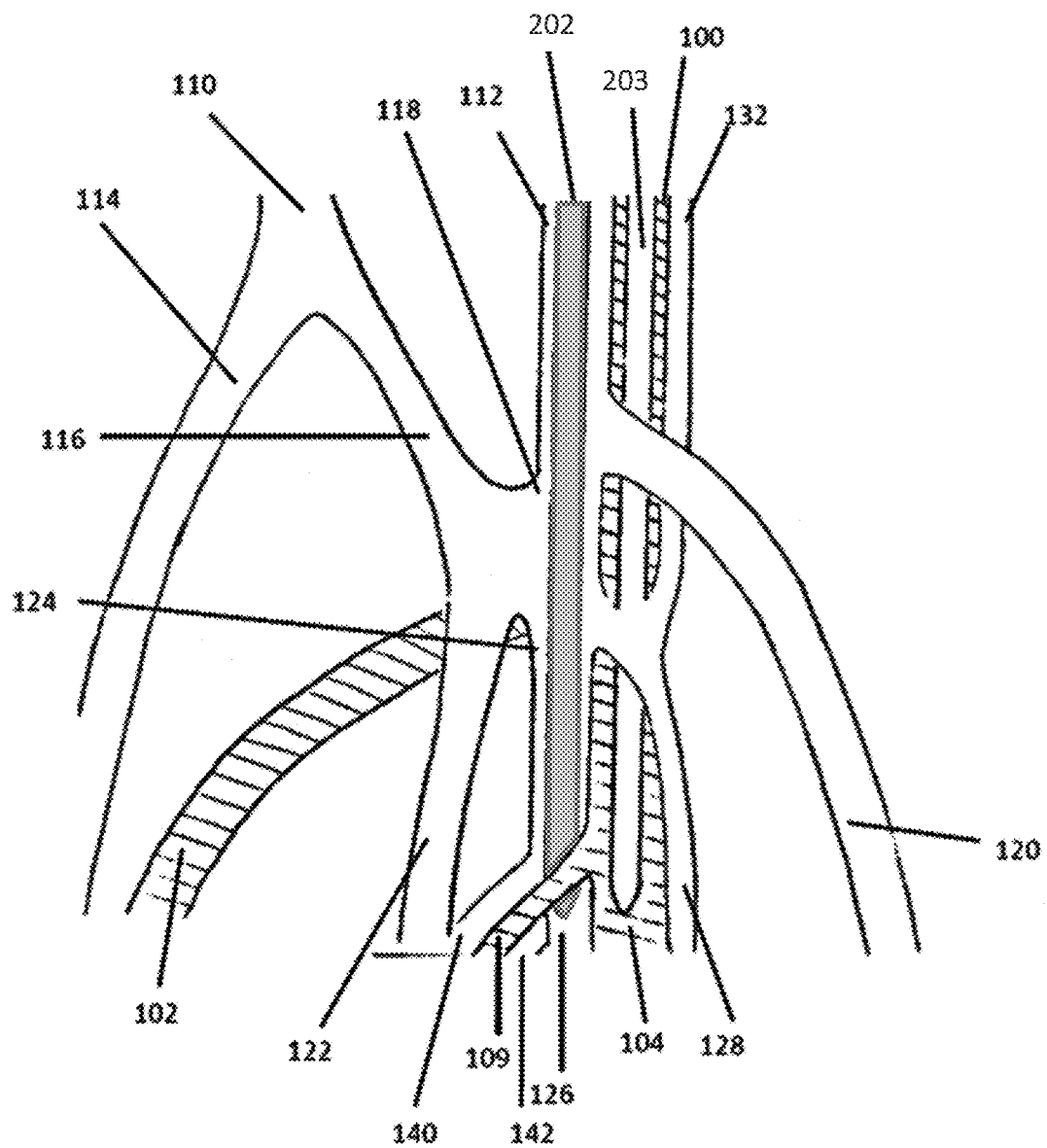
Figure 3C:
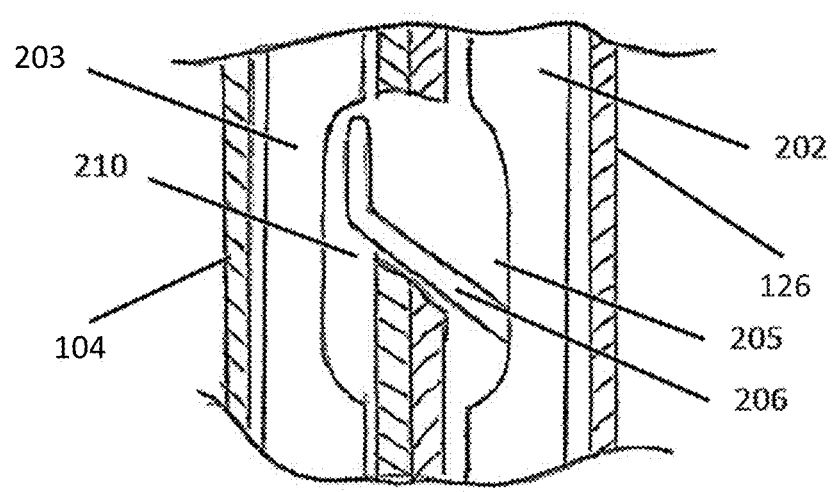

FIGS. 3A-3C depict an illustrative method by which a catheter system (e.g., catheter system (200) of FIG. 2) may be used to form a fistula between a vein and an artery to lower blood pressure. The labeling of FIGS. 1 and 2 will be used for common elements and anatomical locations. The method is described here with reference to forming a fistula between a first deep ulnar vein and an ulnar artery, but it should be understood that the method can similarly be performed to form a fistula between a radial artery and a radial vein, or any suitable artery and vein.

As shown in FIG. 3A, the method may comprise endovascularly advancing a distal portion of a second catheter (203) into an ulnar artery (104). In the method shown in FIGS. 3A-3C, the second catheter (203) may be advanced into the ulnar artery (104) from the brachial artery (100). In some variations, the method may comprise creating an access site (not shown) in the brachial artery (100), and advancing the second catheter (203) into the brachial artery (100) through the access site. It should be appreciated, however, that the second catheter (203) may be advanced into the ulnar artery in any suitable manner, as described in more detail below.

As shown in FIG. 3B, the method may comprise endovascularly advancing a first catheter (202) into a first deep ulnar vein (126). (It should be appreciated that the first catheter (202) may be advanced into either of the deep ulnar veins (126) or (128)). In the method shown in FIG. 3B, the first catheter (202) may be advanced into the first deep ulnar vein (126) from the perforating branch (124), which may be accessed by advancing the first catheter (202) through the basilic vein (112) and the median cubital vein (118). In some variations, the method may comprise creating an access site (not shown) in the basilic vein (112), and advancing the first catheter (202) into the basilic vein (112) through the access site. It should be appreciated, however, that the first catheter (202) may be advanced into the deep ulnar vein (126) in any suitable manner, as described in more detail herein. While the second catheter (203) is shown in FIG. 3A as being advanced into ulnar artery (104) prior to advancement of the first catheter (202) into the deep ulnar vein (126), it should be appreciated that the first (202) and second (203) catheters may be advanced in any order.

Once the distal ends of the first (202) and second (203) catheters have been advanced into the deep ulnar vein (126) and the ulnar artery (104), the first (202) and second (203) catheters may be axially positioned relative to one another to align the opening (205) of the first catheter (202) with the recess (210) of the second catheter (203), as shown in FIG. 3C. Additionally, the first (202) and second (203) catheters may be axially positioned relative to the deep ulnar vein (126) and ulnar artery (104) respectively such that the opening (205) of the first catheter (202) and recess (210) of the second catheter (203) are axially aligned with the desired fistula formation site. In some instances, when the opening (205) of the first catheter (202) and recess (210) of the second catheter (203) are axially aligned with the desired fistula formation site (e.g., in a ulnar artery and a deep ulnar vein), the distal tips of the first and second catheters may extend into the deep ulnar vein (126) and the ulnar artery (104) distally of the branching of the interosseous artery (109) and the interosseous veins (e.g. the first interosseous vein (140)), such as shown in FIG. 3B. Alternatively, when the opening (205) of the second catheter (203) and recess (210) of the first catheter (202) are axially aligned as discussed above, a distal tip of the second catheter (203) may extend into the interosseous artery (109) and/or the distal tip of the first catheter (202) may extend into an interosseous vein (e.g., first interosseous vein (140)).

Additionally, the first (202) and second (203) catheters may be rotationally aligned such that opening (205) of the first catheter (202) may face the recess (210) of the second catheter (203). As mentioned above, in some variations, the methods may comprise using one or more magnetic alignment elements help achieve the axial or rotational positioning of the first (202) and second (203) catheters. Additionally or alternatively, the positioning of the first (202) and second (203) catheters may be confirmed by visualizing markers of the first and/or second catheters.

Access to a vascular site may be achieved in any suitable manner. In variations where a catheter is advanced endovascularly into the ulnar artery, access to the ulnar artery may be achieved in any suitable manner. In some variations, for example, the catheter may be advanced along the brachial artery and into the ulnar artery. In some of these methods, the catheter may be introduced into the vasculature via a brachial access site. In some of these methods, the brachial artery may be cannulated with a cannula directed distally in the brachial artery. The cannula may be any suitable size (e.g., about 5 Fr, about 7 Fr, between about 5 Fr and about 7 Fr), and may be introduced into the brachial access site in any suitable manner, for example, using the Seldinger technique, a micropuncture set, and/or a cutdown procedure. In other variations, the catheter may be advanced along the brachial artery from an access site upstream of the brachial artery. For example, the catheter may be introduced into the vasculature via a femoral artery access site, and may be advanced to the brachial artery therefrom.

In some variations where a catheter is advanced endovascularly into the ulnar artery, the ulnar artery may be accessed directly. In some of these variations, an ulnar access site may be formed in the ulnar artery (e.g., at a distal location in the wrist or forearm where the ulnar artery is superficially positioned), and a catheter may be advanced in a retrograde fashion through the ulnar access site. In these variations, the ulnar artery may be cannulated as described above. In still other variations, a catheter or other tool may be advanced endovascularly into the ulnar artery through an access site in the radial artery. In some variations, arterial access sites may include the distal radial artery at the wrist, the distal ulnar artery at the wrist, the proximal brachial artery, the femoral artery, the subclavian artery, or the tibial artery. The catheter may be advanced into the ulnar artery using one or more visualization techniques (e.g., via fluoroscopy, ultrasound, combinations thereof, or the like). In some variations, the catheter may be advanced over or along a guidewire which may be placed at the target fistula formation site via one or more of the vascular access sites.

In variations where a catheter or other tool is advanced endovascularly into a deep ulnar vein, access to the deep ulnar vein may be achieved in any suitable manner. In some variations, the catheter may be introduced into the vascular site via an access site. A vascular access site may be formed using a micropuncture set, an access needle (e.g., a 18 or 19 gauge access needle), and/or using a surgical cut-down procedure, such that a cannula may be placed in the blood vessel. The venous access site may be in any suitable blood vessel, such as the basilic vein, the cephalic vein, or a brachial vein.

In some variations, the catheter may be advanced to a deep ulnar vein endovascularly along the median cubital vein. For example in some variations, the catheter may be advanced along the basilic vein, into the median cubital vein, and into one of the deep ulnar veins via the perforating branch extending between the median cubital vein and the deep ulnar veins. In instances where the perforating branch extends between the deep ulnar veins and the median antebrachial vein, the catheter may be advanced from the median cubital vein into the median vein, then into one of the deep ulnar veins. In other variations, the catheter may be advanced to a deep ulnar vein endovascularly along the median cephalic vein. For example, in some variations, the catheter may be advanced into the vasculature through an access site in the cephalic vein, and may be endovascularly advanced from the cephalic vein into the median cephalic vein, and into one of the deep ulnar veins via a perforating branch (to access the perforating branch, it may be necessary to advance the catheter into either the median cubital vein or the median antebrachial vein). In still other variations, the catheter may be advanced to a deep ulnar vein endovascularly along a brachial vein. For example, in some variations, the catheter may be advanced into the vasculature through an access site in a brachial vein, and may be endovascularly advanced from the brachial vein into one of the deep ulnar veins in a retrograde fashion. In some variations, venous access sites may include the distal radial vein, the distal ulnar vein, the brachial vein, the subclavian vein, the internal jugular vein, the femoral vein, the basilic vein, the cephalic vein, or the tibial vein.

The catheter may be advanced into the deep ulnar vein using one or more visualization techniques (e.g., via fluoroscopy, ultrasound, combinations thereof, or the like). In some variations, the catheter may be advanced over or along a guidewire which may be placed at the target fistula formation site via one or more of the vascular access sites.

Additionally or alternatively, the methods may comprise visualizing one or more markers from one or more catheters during advancement and positioning thereof. In some variations, the marker may be directly visualized. In other variations, the marker may be indirectly visualized (e.g., via ultrasound, fluoroscopy and/or X-ray visualization). For example, in variations where a method comprises axially aligning the opening (205) of the first catheter (202) relative to the recess (210) of the second catheter (203) and/or rotationally aligning the opening (205) of the first catheter (202) relative to the recess (210) of the second catheter (203), the method may further comprise visualizing one or more markers (214) of the first (202) and/or second (203) catheters to confirm this positioning.

After catheter advancement, one or more fistula-forming elements may be used to create one or more fistulas between two blood vessels. For example, in some variations, one of the first and second catheters may comprise a fistula-forming element (e.g., an electrode), while the other catheter does not comprise a fistula-forming element. In other variations, both catheters may comprise a fistula-forming element. In some of these variations, the fistula-forming elements of the first and second catheters may act to form different fistulas or in combination to form the same fistula. In some variations, radiofrequency energy is applied to one or more electrodes of one or more catheters to ablate or otherwise vaporize tissue as current passes therethrough.

In some variations, the electrode has a configuration to form one or more fistulas having fistula characteristics selected as described above to provide a desired blood pressure. For example, the electrode may be configured to form a fistula having a desired fistula size and shape, as discussed in more detail above. In other variations, the electrode may be configured to form a plurality of fistulas between two vessels, having a desired size, shape, and relative position. Returning to the method of FIGS. 3A-3C, in one variation, once the first (202) and second (203) catheters are positioned relative to each other and their respective vessels, the electrode (206) may be advanced out of the opening (205) of the first catheter (202) to press the electrode (206) against a vessel wall of the deep ulnar vein (126). Energy may be delivered to the electrode (206) to cut tissue, which may advance the electrode (206) from the deep ulnar vein (126), through the wall of the ulnar artery (104), and into the ulnar artery (104). It should be appreciated that in other variations, the first catheter (202) comprising the electrode (206) may be placed in the ulnar artery (104) and the second catheter (203) may be placed in the deep ulnar vein (126), such that the electrode (206) may be advanced from the ulnar artery (104) into the deep ulnar vein (126). It should be appreciated that in variations of catheter systems in which both the first and second catheters comprise fistula-formation elements (e.g., electrodes), energy may be delivered by both electrodes to cut tissue, and/or current may be delivered from one electrode to the other.

After formation of a first fistula, one or more additional fistulas may be formed. In some variations, one or more additional fistulas may be formed by moving the first and second catheters to a new location and repeating the procedure described herein. For example, based on a desired amount of blood pressure reduction, a single fistula or a plurality of fistulas may be formed, as described in more detail herein. Multiple fistulas may be formed in one artery-vein pair or multiple artery-vein pairs. For example, if a user or physician determines that there is insufficient flow between an ulnar artery and a first deep ulnar vein, a second fistula may be formed between an ulnar artery and a second deep ulnar vein. The second fistula may be formed during the same procedure, or may be formed during a subsequent procedure. In variations where multiple fistulas are formed, the fistulas may have the same or different characteristics (e.g., size, shape, etc.). In one variation, a series of fistulas may be formed axially along the blood vessels.

Following activation of an electrode, one or more steps may be conducted to confirm fistula formation. For example, in some variations a radiopaque dye (or other suitable contrast media) may be introduced into the artery to confirm blood flow into the vein from the artery following activation of the fistula-forming element. For instance, in the example of FIGS. 3A-3C, once the fistula has been has been formed between the ulnar artery (104) and the deep ulnar vein (126), one or more contrast agents may be passed through the fistula between the ulnar artery (104) and ulnar vein (126).

In some variations, it may be desirable for the formed fistula(s) to have particular flow rates based on a desired blood pressure reduction. For instance, a fistula with flow rates exceeding approximately 300 ml/min may have a measurable effect on systolic and diastolic pressure. In some variations, it may be desirable for the flow rate through the fistula(s) to be between about 300 mL/min and about 1500 mL/min. In some of these variations, it may be desirable for the flow rate through the fistula to be about 1000 mL/min. In some cases, the desired flow rate may be dependent on the body-mass index of the patient. It should also be appreciated that in some variations, the desired flow rate may depend not only on the absolute desired reduction in blood pressure, but on a patient's initial blood pressure.

It should be appreciated that in some or all of the methods described here, one or more portions of the patient may be immobilized during some all of the steps of the method. For example, when a fistula is formed between two vessels in an arm, one or more portions of the arm (e.g., a wrist, an elbow, or the like) may be immobilized. In some of these variations, a wrist of the patient may be immobilized. When a wrist is immobilized, the wrist may be immobilized prior to creating access to one or more blood vessels. In some of these variations, the wrist may remain immobilized until after formation of the fistula. It should be appreciated that when a portion of the arm is immobilized, the arm may be temporarily released to reposition the arm, if needed.

Vessel Modification

In some cases, a fistula may stretch during maturation due to the elasticity of the tissue and the increased blood flow through the fistula after formation. As a fistula matures over time (e.g., weeks or months), the fistula may undergo enlargement or dilation. This enlargement or dilation may be a function of vessel composition and a rate of fluid flow through the fistula. For example, fistulas located in muscular arteries may resist dilation more so than elastic arteries. In some cases, a fistula may undergo dilation due to high blood flow through the fistula. Enlargement or dilation of a fistula over time may change a rate of blood flow and cause a corresponding change in the blood pressure. In some variations of the methods described herein, a fistula may be initially formed smaller to account for later enlargement or dilation during maturation. In other variations of the methods described herein, enlargement or dilation of a fistula over time may be undesirable. As such, it may in some instances be beneficial for the method to comprise steps configured to reduce or counteract enlargement or dilation during maturation.

In some variations, the methods described herein may comprise modifying elasticity and/or size of one or more blood vessels such as through vessel heating. Additionally or alternatively, the methods described herein may comprise placing a stent in a vessel proximal to a fistula. These methods of modifying the vessels may be performed prior to fistula formation or after fistula formation. In some cases, tuning blood pressure reduction to a desired level may be more easily performed by reducing fistula flow after an initial blood pressure drop. In other words, a fistula may be formed that is intended to overshoot a desired blood pressure reduction. Vessel modification may thereafter be performed as a secondary procedure for titrating blood flow to increase blood pressure to a desired blood pressure such as by shrinking or occluding a vessel, as described in more detail herein.

Figure 6A:
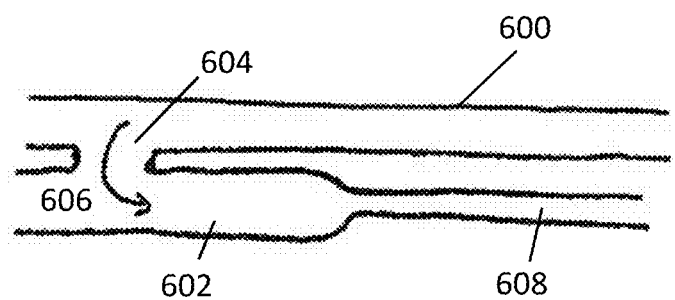
FIGS. 6A-6C are side and cross-sectional views of illustrative methods of vessel shrinking.
Figure 6B:
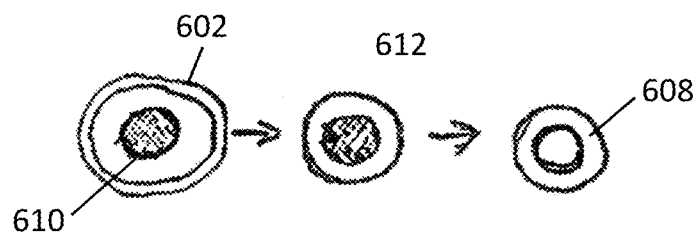
Figure 6C:
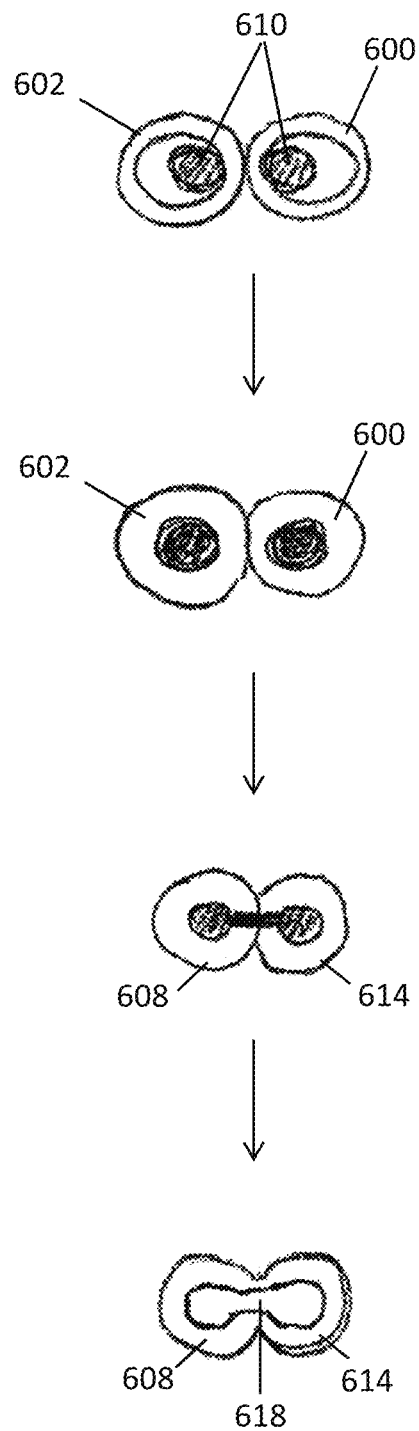

In some variations, modification of one or more vessels may comprise shrinking and reducing the elasticity of one or more blood vessels. The lower elasticity of tissue of a shrunken vessel may reduce post-fistula stretching. Additionally or alternatively, constriction of a portion of a blood vessel proximal to a fistula may increase the proximal resistance of the vessel. An example is shown in FIGS. 6A-6C. FIG. 6A illustrates a fistula (604) formed between an artery (600) and vein (602) having an arterial inflow (606) and a shrunken vein portion (608) proximal to the fistula (604). Vessel shrinkage proximal to the fistula (604) in one or both of the artery (600) and the vein (602) may reduce flow rate. FIG. 6B illustrates a cross-sectional view of a vein (602) undergoing heating by a catheter (610), where heat (612) generated by the catheter induces collagen denaturing and subsequent constriction to form a shrunken vein (608) having decreased elasticity. A predetermined catheter diameter and length may be provided to heat and shrink a desired portion of a vessel to a desired diameter and length. The catheter may be applied with coagulation energy to induce a collagen shrink response rather than a cutting energy.

Vessel shrinkage is not particularly limited with respect to fistula formation and may be performed before or after fistula formation. For instance, a portion of a blood vessel proximal to a fistula may be constricted as a secondary intervention to reduce fistula flow and increase blood pressure. In other variations of the methods described herein, modification of one or more vessels may comprise shrinking a fistula site prior to forming the fistula. Pre-shrinking one or more vessels may create a thicker and stiffer tissue bed for an electrode to cut through to form one or more fistulas. After a fistula is formed, the thicker tissue around the fistula may provide improved resistance to enlargement.

For example, FIG. 6C provides a cross-sectional view of an artery (600) and a vein (602) each having a catheter (610) disposed within the vessel for heating it. As heat is applied to the vessels by the catheters (610), the artery (600) and vein (602) may shrink until their diameters match those of the catheters (610). Then, either the same or different catheters may be used to cut a fistula between the shrunken artery (614) and shrunken vein (608). The shrunken vein (608), shrunken artery (614), and fistula (604) are less likely to stretch and expand after formation of the fistula (604) and the removal of the catheters. In some variations, low voltage Joule heating may be applied to the tissue with the electrode. In some cases, it may be desirable to heat the tissue to a temperature between about 60° C. and about 80° C., since collagen may denature and shrink around these temperatures.

Figure 7A:
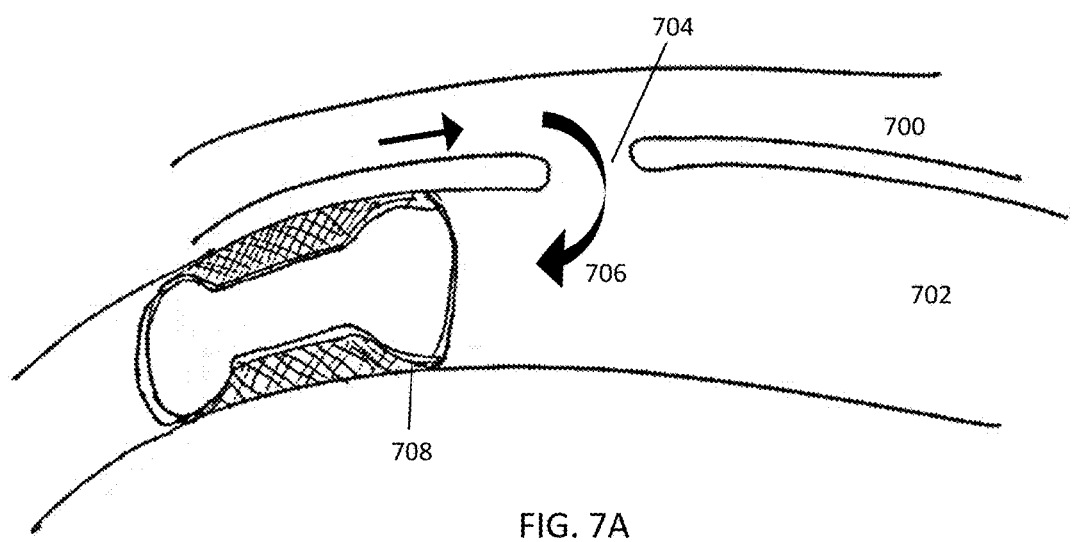
FIGS. 7A-7B are cross-sectional side views of illustrative methods of modifying a vessel.
Figure 7B:
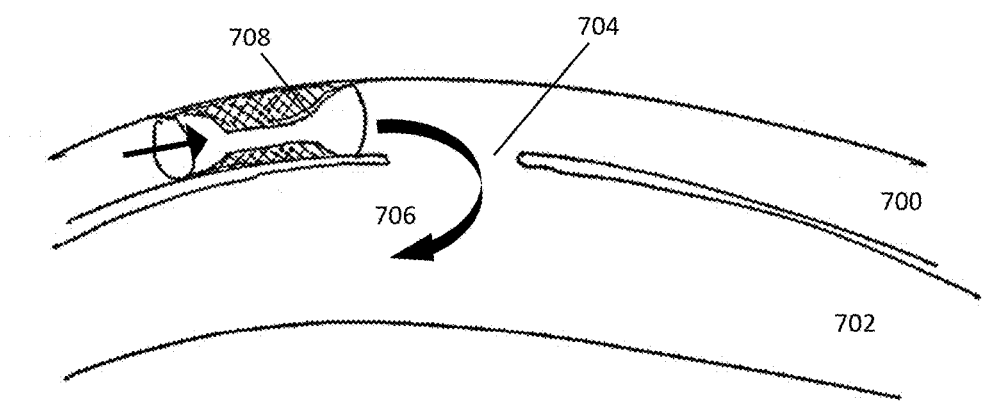

Additionally or alternatively, modification of one or more vessels may comprise inserting a stent proximal to a fistula in one or more blood vessels. An example is shown in FIG. 7A. As shown there, a fistula (704) may be located between an artery (700) and vein (702) with an arterial inflow (706). A stent (708) may be placed (e.g., deployed by a catheter) in the vein (702) proximal to the fistula (704) to provide venous restriction of blood flow, which may reduce blood flow through the vessel and in turn through the fistula. FIG. 7B illustrates a stent (708) placed (e.g., deployed by a catheter) in the artery (700) proximal to the fistula (704) to restrict arterial inflow (704). A stent may thus modify the vessel to change a blood pressure of a patient. In some cases, a stent may be deployed as a secondary intervention to increase blood pressure after fistula formation and/or fistula maturation. In other cases, a stent may be provided proximal to a fistula site prior to fistula formation to pre-emptively reduce fistula growth due to high blood flow through the fistula.

Additionally or alternatively, modification of one or more vessels may comprise occluding the fistula. For instance, one or more of a covered stent and embolization plug or coil may be used to occlude one or more fistulas. This may be useful where multiple fistula are formed and a resultant flow rate between the vessels is too high. In some cases, occluding one or more of the fistulas may increase blood pressure by a desired amount. One or more of the fistulas may be totally and/or partially occluded based on a desired increase in blood pressure.

III. Example

Figure 8A:
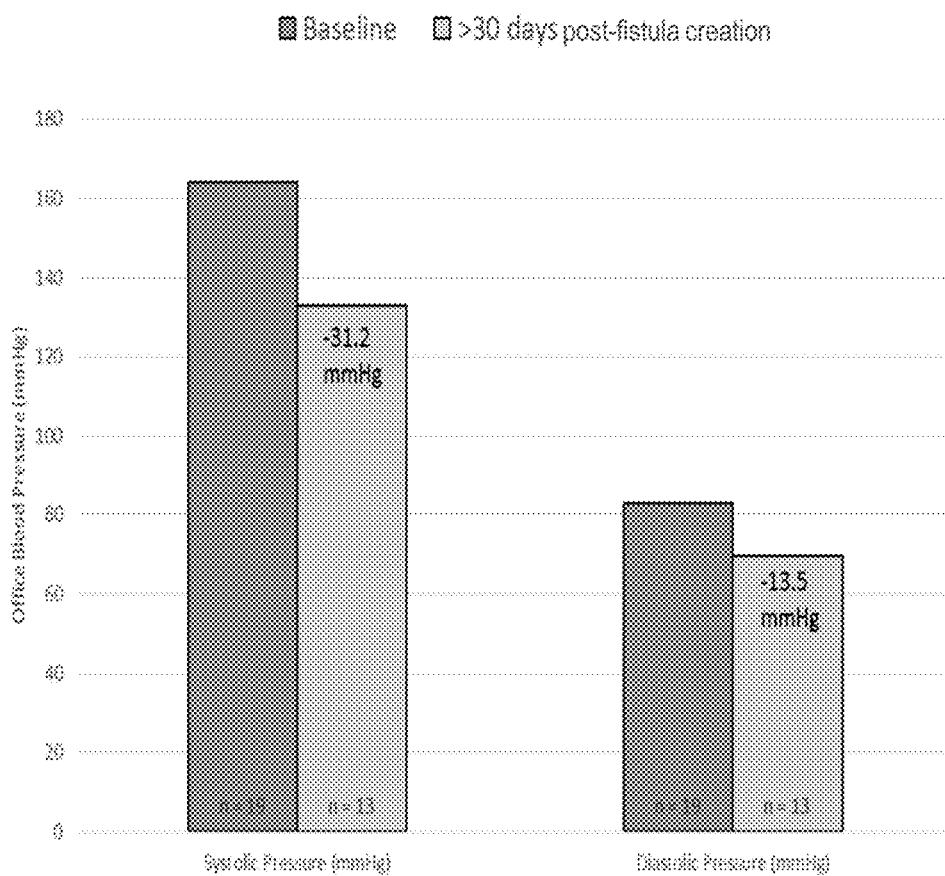
FIGS. 8A-8B are illustrative graphs depicting changes in blood pressure for a group of hypertensive patients after fistula formation.
Figure 8B:
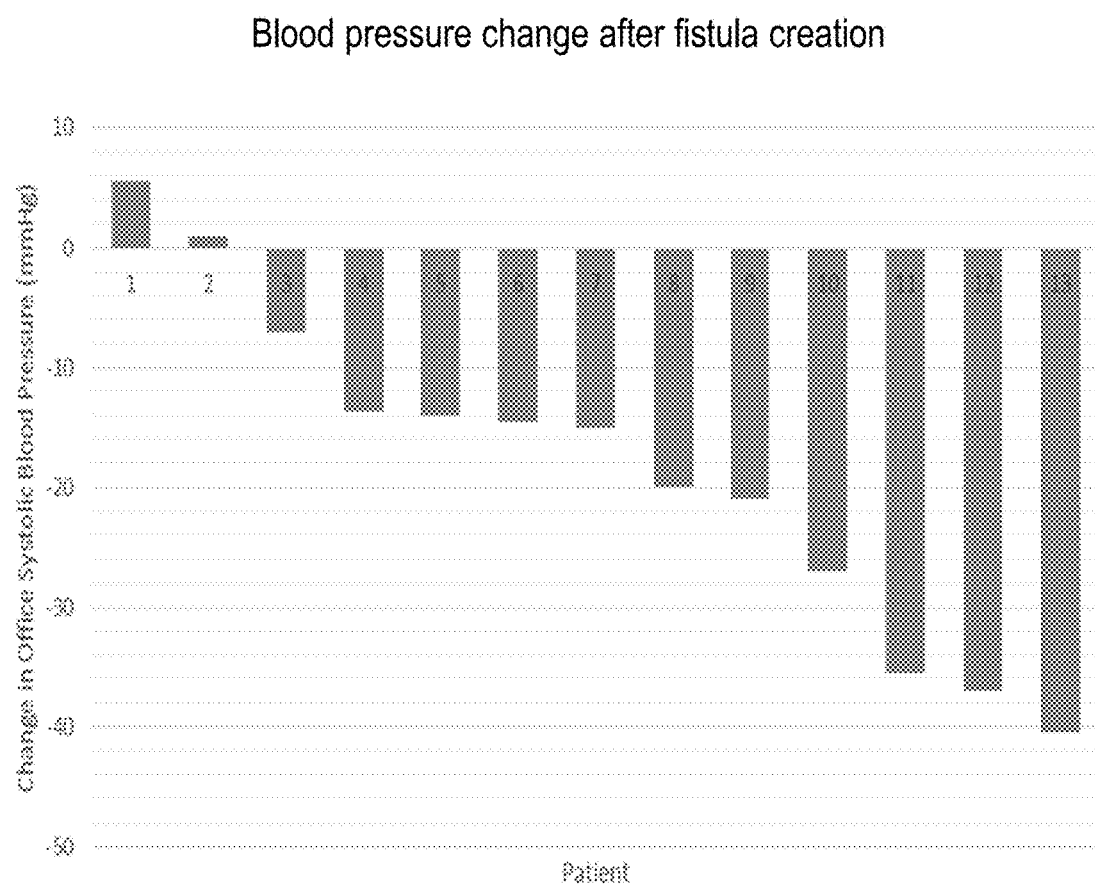

FIGS. 8A-8B are illustrative bar graphs of changes in blood pressure for a group of hypertensive patients after fistula formation using the methods described above. FIG. 8A illustrates systolic blood pressure and diastolic blood pressure for patients before and after undergoing a procedure to receive a percutaneously-formed fistula between a proximal ulnar artery and a deep ulnar vein of an arm. Nineteen hypertensive patients having baseline systolic blood pressure over 150 mmHg underwent fistula formation. To form the fistula, a first catheter carrying an electrode was percutaneously positioned in the deep ulnar vein (via brachial vein access) and a second catheter was percutaneously positioned in the proximal ulnar artery (via brachial artery access). The electrode was used to ablate tissue between the deep ulnar vein and the proximal ulnar artery to remove the tissue between the vessels. The arm was immobilized at the wrist during the formation of the fistula.

The blood pressure of the patients was measured before and 30 days after fistula formation. As shown in FIG. 8A, before fistula formation, the nineteen patients had a mean baseline initial systolic blood pressure of approximately 165 mmHg and a mean diastolic blood pressure of approximately 83 mmHg. Thirteen of the nineteen patients had reached the 30-day follow-up at the time of analysis. (Six of the nineteen patients had their fistulas formed fewer than 30 days prior to analysis.) As measured at the 30-day follow-up, these thirteen patients experienced a mean drop in systolic blood pressure of 31.2 mmHg (about 19%) and a mean drop in diastolic blood pressure of 13.5 mmHg (16%).

FIG. 8B shows the change in systolic blood pressure for each of the thirteen patients measured at the 30-day follow-up. Some patients experienced a systolic blood pressure decrease of more than 30 mmHg, including about 40 mmHg. Some patients experienced a reduction in systolic blood pressure of about at least 15% from baseline systolic blood pressure. Some patients having a baseline systolic blood pressure of about at least 170 mmHg experienced a reduction in systolic blood pressure of about at least 20% from the baseline systolic blood pressure.

Although the foregoing implementations has, for the purposes of clarity and understanding, been described in some detail by of illustration and example, it will be apparent that certain changes and modifications may be practiced, and are intended to fall within the scope of the appended claims. Additionally, it should be understood that the components and characteristics of the devices described herein may be combined and interchanged as appropriate, the steps of the methods described herein may be combined and interchanged as appropriate, and any of the devices described herein may be used in the methods described herein as appropriate. The description of certain elements, characteristics, or steps with respect to a specific figure are not intended to be limiting or nor should they be interpreted to suggest that the element cannot be used in combination with any of the other described elements.

We claim:

1. A method of treating a patient having hypertension comprising:
   advancing a first catheter into a first deep ulnar vein and a second catheter into an artery, wherein the first catheter comprises an electrode, the first deep ulnar vein being substantially parallel to a proximal ulnar artery between a brachial artery and an interosseous artery; and
   forming a first fistula between the first deep ulnar vein and the artery with the electrode to reduce a blood pressure of the patient.

2. The method of claim 1 further comprising determining a desired amount of blood pressure reduction, and forming the first fistula based on the desired amount of blood pressure reduction.

3. The method of claim 1 wherein the artery is the proximal ulnar artery.

4. The method of claim 1 further comprising forming a second fistula between the artery and a second deep ulnar vein.

5. A method of treating a patient having hypertension comprising:
   advancing a first catheter into a first deep ulnar vein and a second catheter into an artery, wherein the first catheter comprises an electrode, the first deep ulnar vein being substantially parallel to a proximal ulnar artery between a brachial artery and an interosseous artery;
   forming a fistula between the first deep ulnar vein and the artery with the electrode, wherein the fistula is configured to reduce blood pressure of the patient below a desired blood pressure; and
   modifying one or more of the first deep ulnar vein and the artery to increase the blood pressure to the desired blood pressure.

* * * * *